(12) United States Patent
Covello et al.

(10) Patent No.: US 10,513,701 B2
(45) Date of Patent: Dec. 24, 2019

(54) RNA INTERFERENCE MEDIATED THERAPY FOR NEURODEGENERATIVE DISEASES

(71) Applicant: UNIVERSITÀ DEGLI STUDI DI TRENTO, Trento (IT)

(72) Inventors: Giuseppina Covello, Trento (IT); Michela Alessandra Denti, Trento (IT); Kavitha Siva, Chennai (IN)

(73) Assignee: UNIVERSITÀ DEGLI STUDI DI TRENTO, Trento (IT)

( * ) Notice: Subject to any disclaimer, the term of this patent is extended or adjusted under 35 U.S.C. 154(b) by 0 days.

(21) Appl. No.: 15/561,208

(22) PCT Filed: Mar. 24, 2016

(86) PCT No.: PCT/IB2016/051676
§ 371 (c)(1),
(2) Date: Sep. 25, 2017

(87) PCT Pub. No.: WO2016/151523
PCT Pub. Date: Sep. 29, 2016

(65) Prior Publication Data
US 2018/0066254 A1    Mar. 8, 2018

(30) Foreign Application Priority Data
Mar. 25, 2015  (IT) .............................. TO2015A0185

(51) Int. Cl.
*C12N 15/113* (2010.01)
*A61K 31/713* (2006.01)
*C12N 5/00* (2006.01)

(52) U.S. Cl.
CPC .......... *C12N 15/113* (2013.01); *A61K 31/713* (2013.01); *C12N 2310/14* (2013.01); *C12N 2310/315* (2013.01); *C12N 2310/3515* (2013.01); *C12N 2310/3533* (2013.01)

(58) Field of Classification Search
None
See application file for complete search history.

(56) References Cited

U.S. PATENT DOCUMENTS

| 2003/0170704 A1 | 9/2003 | Stamm et al. |
| 2009/0176728 A1 | 7/2009 | Yague et al. |
| 2016/0032285 A1* | 2/2016 | Rigo .................... C12N 15/113 514/44 A |

FOREIGN PATENT DOCUMENTS

| WO | WO 01/32703 | 5/2001 |
| WO | WO 2007/107789 | 9/2007 |
| WO | WO 2014/153236 | 9/2014 |
| WO | WO 2015/010135 | 1/2015 |

OTHER PUBLICATIONS

International Search Report for PCT/IB2016/051676, dated Jun. 1, 2016, 7 pages.
Written Opinion of the ISA for PCT/IB2016/051676, dated Jun. 1, 2016, 8 pages.
Zhou Jianhua et al., "Alternative splicing of exon 10 in the tau gene as a target for treatment of tauopathies", BMC Neuroscience, vol. 9, No. Suppl 2, Dec. 3, 2008, pp. 1-8.
Kalbfuss et al., "Correction of Alternative Splicing of Tau in Frontotemporal Dementia and Parkinsonism Linked to Chromosome 17", Journal of Biological Chemistry, vol. 276, No. 46, Nov. 9, 2001, pp. 42986-42993.
Covello, "Antisense RNA-induced exon-skipping for the gene therapy of frontotemporal dementia and parkinsonism associated with chromosome 17 (FTDP-17)", FEBS Journal, Sep. 2012, vil. 279, No. Suppl. 1 Iss, SI, p. 509.
Xu Hong et al., "Tau Silencing by siRNA in the P301S Mouse Model of Tauopathy", Current Gene Therapy vol. 14, No. 5, Oct. 1, 2014, pp. 343-351.
Sud et al., "Antisense-mediated Exon Skipping Decreases Tau Protein Expression: A Potential Therapy for Tauopathies", Molecular Therapy—Nucleic Acids, vol. 3, E180, Jul. 29, 2014, pp. 1-11.
Miller et al., "Targeting Alzheimer's disease genes with RNA interference: An efficient strategy for silencing mutant alleles", Nucleic Acids Research, vol. 32, No. 2, Jan. 30, 2004, pp. 661-668.
Stoilov et al. A high-throughput screening strategy identifies cardiotonic steroids as alternative splicing modulators. Proc Natl Acad Sci U S A (2008) 105(32): 11218-23.
Rodriguez-Martin et al. Correction of tau mis-splicing caused by FTDP-17 MAPT mutations by spliceosome-mediated RNA trans-splicing. Hum Mol Genet (2009) 18(17): 3266-73.
Cashman et al. Neuroblastoma x spinal cord (NSC) hybrid cell lines resemble developing motor neurons. Dev Dyn (1992); 194(3):209-21.
Maier et al. Differentiated NSC-34 motoneuron-like cells as experimental model for cholinergic neurodegeneration. Neurochem Int (2013) 62(8): 1029-38 9.
McCormack et al., Alpha-synuclein suppression by targeted small interfering RNA in the primate substantia nigra. PLoS One 5: el2122, 2010.
Wang et al. Therapeutic gene silencing delivered by a chemically modified small interfering RNA against mutant SOD1 slows amyotrophic lateral sclerosis progression. J Biol Chem 283:, 2008, 15845-15852.
Difiglia et al. Therapeutic silencing of mutant huntingtin with siRNA attenuates striatal and cortical neuropathology and behavioral deficits. Proc Natl Acad Sci USA (2007) 104: 17204-17209.
Senechal et al. (2007). Amyloid precursor protein knockdown by siRNA impairs spontaneous alternation in adult mice. J Neurochem 102: 1928-1940.
Rettig GR, Behlke MA Progress toward in vivo use of siRNAs-II Mol Ther. Mar. 2012;20 (3):483-512.
Kandhavelu et al., FEBS Journal, vol. 279, No. Suppl. 1, Sp. Iss. SI, P22-11 Sep. 2012 (Sep. 2012), p. 509.

(Continued)

*Primary Examiner* — Sean McGarry
(74) *Attorney, Agent, or Firm* — Nixon & Vanderhye P.C.

(57) ABSTRACT

Therapeutic agent for use in the treatment of neurodegenerative diseases associated with abnormalities of MAPT gene encoded protein tau, wherein said therapeutic agent comprises one or more siRNAs targeting MAPT exon 10 sequence.

19 Claims, 15 Drawing Sheets

Specification includes a Sequence Listing.

(56) References Cited

OTHER PUBLICATIONS

Wood M, et al., "Modulating the Expression of Disease Genes with RNA-Based Therapy," PLoS Genetics 3: e109 (2007).
Nishikura K, "A Short Primer on RNAi: RNA-Directed RNA Polymerase Acts as a Key Catalyst," Cell, vol. 107:415-418 (2001).
Robb, et al., "Specific and potent RNAi in the nucleus of human cells," Nat Structural Molecular Biology, vol. 12:133-7 (2005).
Zhang, et al., "RNA interference, a potential strategy for isoform-specific phosphatidylinositol 3-kinase targeted therapy in ovarian cancer," Cancer Biology & Therapy, 3: 1283-1289 (2004).
Shen, et al., "Vector-based RNAi approach to isoform-specific downregulation of vascular endothelial growth factor (VEGF)165 expression in human leukemia cells," Leukemia Research 31: 515-521 (2007).
Banda, et al., "Targeting of Liver Mannan-Binding Lectin-Associated Serine Protease-3 with RNA Interference Ameliorates Disease in a Mouse Model of Rheumatoid Arthritis," Immunohorizons. 2: 274-295. doi:10.4049/immunohorizons.1800053 (2018).
Watts, et al., "Gene silencing by siRNAs and antisense oligonucleotides in the laboratory and the clinic," *J Pathol.* 226: 365-379. doi:10.1002/path.2993 (2012).
Elbashir, et al., "RNA interference is mediated by 21-and 22-nucleotide RNAs," Genes & Development 15:188-200 (2001).

\* cited by examiner

```
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta acaactccgc cccattgacg caaatgggcg gtaggcgtgt   540
acggtgggag gtctatataa gcagagctgg tttagtgaac cgtcagatcc gctagcgcta   600
ccggactcag atctaccatt ggtgcacctg actcctgagg agaagtctgc gttactgcc   660
ctgtggggca aggtgaacgt ggaagagttg gtggtgaggc cctgggccac cagtaagtat   720
caaggttaca agacaggttt aaggagacca atagaaactg ggcatgtgga gacagagaag   780
actcttgggt ttctgaattc ctcatccttt tttctggcta ccaaaggtgc agataattaa   840
taagaagctg gatcttagca acgtccagtc caagtgtggc tcaaaggata atatcaaaca   900
cgtcccggga ggcggcagtg tgagtacctt cacgcgtccc atgcgccgtg ctgtggcttg   960
aattattagg aagtggtgtg agtgcgtaca cttgcgagac actgcataga ataaatcctt  1020
ctggatccac catggtggct agatccggg catgtggaga cagagaagac tgttgagttt   1080
gtgataagca ctgactctct ctgcctattg gtctattttc cctccctcag tggcggtcga  1140
ggacaaactc tacgcggact tgccagtacg cttcgtgagc aagggcgagg agctgttcac  1200
cggggtggtg cccatcctgg tcgagctgga cggcgacgta acggccaca agttcagcgt   1260
gtccggcgag ggcgagggcg acgccaccta cggcaagctg accctgaagt tcatctgcac  1320
caccggcaag ctgcccgtgc cctggcccac cctcgtgacc accctgacct acggcgtgca  1380
gtgcttagc cgctaccccg accacctgaa gcagcacgac ttcttcaaga gtgcaatgcc   1440
cgaaggctac gtccaggagc gcaccatctt cttcaaggac gacggcaact acaagacccg  1500
cgccgaggtg aagttcgagg gcgacaccct ggtgaaccgc atcgagctga agggcatcga  1560
cttcaaggag gacggcaaca tcctggggca aagctggag tacaactaca acagccacaa  1620
cgtctatatc accgccgaca agcagaagaa cggcatcaag gtgaacttca gatccgcca   1680
caacatcgag gacggcagcg tgcagctcgc cgaccactac cagcagaaca ccccatcgg   1740
cgacggcccc gtgctgctgc ccgacaacca ctacctgagc acccagtccg ccctgagcaa  1800
agaccccaac gagaagcgcg atcatatggt cctgctggag ttcgtgaccg ccgccgggat  1860
cactctcggc accgacgagc tgtacaagta accggtcgcc accatggtga gcaagggcga  1920
ggagaataac atggccatca tcaaggagtt catgcgcttc aaggtgcgca tggagggctc  1980
cgtgaacggc cacgagttcg agatcgaggg cgagggcgag ggccgcccct acgagggcac  2040
ccagaccgcc aagctgaagg tgaccaaggg tggccccctg cccttcgcct gggacatcct  2100
aaccccccaac ttcacctacg gctccaaggc ctacgtgaag caccccgccg acatccccga  2160
ctacttgaag ctgtccttcc ccgagggctt caagtgggag cgcgtgatga acttcgagga  2220
```

Figure 12

```
cggcggcgtg gtgaccgtga cccaggactc ctccctgcag gacggcgagt tcatctacaa   2280
ggtgaagctg cgcggcacca acttcccctc cgacggcccc gtaatgcaga agaagaccat   2340
gggctgggag gcctcctccg agcggatgta ccccgaggac ggcgccctga agggcgagat   2400
caagatgagg ctgaagctga aggacggcgg ccactacgac gctgaggtca agaccaccta   2460
caaggccaag aagcccgtgc agctgcccgg cgcctacatc gtcggcatca gttggacat   2520
cacctcccac aacgaggact acaccatcgt ggaactgtac gaacgcgccg agggccgcca   2580
ctccaccggc ggcatggacg agctgtataa gtaagcggcc gcgactctag atcataatca   2640
gccataccac atttgtagag gttttacttg ctttaaaaaa cctcccacac ctcccctga   2700
acctgaaaca taaaatgaat gcaattgttg ttgttaactt gtttattgca gcttataatg   2760
gttacaaata aagcaatagc atcacaaatt tcacaaataa agcatttttt tcactgcatt   2820
ctagttgtgg tttgtccaaa ctcatcaatg tatcttaagg cgtaaattgt aagcgttaat   2880
attttgttaa aattcgcgtt aaattttgt taaatcagct cattttttaa ccaataggcc   2940
gaaatcggca aaatcccta taaatcaaaa gaatagaccg atatagggtt gagtgttgtt   3000
ccagtttgga acaagagtcc actattaaag aacgtggact ccaacgtcaa agggcgaaaa   3060
accgtctatc agggcgatgg cccactacgt gaaccatcac cctaatcaag ttttttgggg   3120
tcgaggtgcc gtaaagcact aaatcggaac cctaagggga gcccccgatt tagagcttga   3180
cggggaaagc cggcgaacgt ggcgagaaag gaagggaaga aagcgaaagg agcgggcgct   3240
agggcgctgg caagtgtagc ggtcacgctg cgcgtaacca ccacccgc cgcgcttaat   3300
gcgccgctac agggcgcgtc aggtggcact tttcggggaa atgtgcgcgg aacccctatt   3360
tgtttatttt tctaaataca ttcaaatatg tatccgctca tgagacaata accctgataa   3420
atgcttcaat aatattgaaa aaggaagagt cctgaggcgg aaagaaccag ctgtggaatg   3480
tgtgtcagtt agggtgtgga aagtccccag gctccccagc aggcagaagt atgcaaagca   3540
tgcatctcaa ttagtcagca accaggtgtg gaaagtcccc aggctcccca gcaggcagaa   3600
gtatgcaaag catgcatctc aattagtcag caaccatagt cccgccccta actccgccca   3660
tcccgcccct aactccgccc agttccgccc attctccgcc catggctga ctaatttttt   3720
ttatttatgc agaggccgag gccgcctcgg cctctgagct attccagaag tagtgaggag   3780
gcttttttgg aggcctaggc ttttgcaaag atcgatcaag agacaggatg aggatcgttt   3840
cgcatgattg aacaagatgg attgcacgca ggttctccgg ccgcttgggt ggagaggcta   3900
ttcggctatg actgggcaca acagacaatc ggctgctctg atgccgccgt gttccggctg   3960
tcagcgcagg ggcgcccggt tcttttgtc aagaccgacc tgtccggtgc cctgaatgaa   4020
ctgcaagacg aggcagcgcg gctatcgtgg ctggccacga cgggcgttcc ttgcgcagct   4080
gtgctcgacg ttgtcactga agcgggaagg gactggctgc tattgggcga agtgccgggg   4140
caggatctcc tgtcatctca ccttgctcct gccgagaaag tatccatcat ggctgatgca   4200
atgcggcggc tgcatacgct tgatccggct acctgcccat tcgaccacca agcgaaacat   4260
cgcatcgagc gagcacgtac tcggatggaa gccggtcttg tcgatcagga tgatctggac   4320
gaagagcatc aggggctcgc gccagccgaa ctgttcgcca ggctcaaggc gagcatgccc   4380
gacggcgagg atctcgtcgt gacccatggc gatgcctgct tgccgaatat catggtggaa   4440
aatggccgct tttctggatt catcgactgt ggccggctgg gtgtggcgga ccgctatcag   4500
```

Figure 12 – cont.

```
gacatagcgt tggctacccg tgatattgct gaagagcttg gcggcgaatg ggctgaccgc     4560
ttcctcgtgc tttacggtat cgccgctccc gattcgcagc gcatcgcctt ctatcgcctt     4620
cttgacgagt tcttctgagc gggactctgg ggttcgaaat gaccgaccaa gcgacgccca     4680
acctgccatc acgagatttc gattccaccg ccgccttcta tgaaaggttg ggcttcggaa     4740
tcgttttccg ggacgccggc tggatgatcc tccagcgcgg ggatctcatg ctggagttct     4800
tcgcccaccc taggggagg ctaactgaaa cacggaagga gacaataccg gaaggaaccc     4860
gcgctatgac ggcaataaaa agacagaata aaacgcacgg tgttgggtcg tttgttcata     4920
aacgcgggt tcggtcccag ggctggcact ctgtcgatac cccaccgaga ccccattggg     4980
gccaatacgc ccgcgtttct ccttttccc cacccaccc ccaagttcg ggtgaaggcc     5040
cagggctcgc agccaacgtc ggggcggcag gccctgccat agcctcaggt tactcatata     5100
tactttagat tgatttaaaa cttcattttt aatttaaaag gatctaggtg aagatccttt     5160
ttgataatct catgaccaaa atcccttaac gtgagttttc gttccactga gcgtcagacc     5220
ccgtagaaaa gatcaaagga tcttcttgag atcctttttt tctgcgcgta atctgctgct     5280
tgcaaacaaa aaaaccaccg ctaccagcgg tggtttgttt gccggatcaa gagctaccaa     5340
ctcttttcc gaaggtaact ggcttcagca gagcgcagat accaaatact gtccttctag     5400
tgtagccgta gttaggccac cacttcaaga actctgtagc accgcctaca tacctcgctc     5460
tgctaatcct gttaccagtg gctgctgcca gtggcgataa gtcgtgtctt accgggttgg     5520
actcaagacg atagttaccg gataaggcgc agcggtcggg ctgaacgggg ggttcgtgca     5580
cacagcccag cttggagcga acgacctaca ccgaactgag atacctacag cgtgagctat     5640
gagaaagcgc cacgcttccc gaagggagaa aggcggacag gtatccggta agcggcaggg     5700
tcggaacagg agagcgcacg agggagcttc caggggaaa cgcctggtat ctttatagtc     5760
ctgtcgggtt tcgccacctc tgacttgagc gtcgattttt gtgatgctcg tcaggggggc     5820
ggagcctatg gaaaaacgcc agcaacgcgg cctttttacg gttcctggcc ttttgctggc     5880
cttttgctca catgttcttt cctgcgttat cccctgattc tgtggataac cgtattaccg     5940
ccatgcat                                                              5948
```

Figure 12 - cont.

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctgg tttagtgaac cgtcagatcc gctagcgcta     600
ccggactcag atctaccatt ggtgcacctg actcctgagg agaagtctgc cgttactgcc     660
ctgtggggca aggtgaacgt ggaagagttg gtggtgaggc cctgggccac cagtaagtat     720
caaggttaca agacaggttt aaggagacca atagaaactg ggcatgtgga gacagagaag     780
actcttgggt ttctgaattc ctcatccttt tttctggcta ccaaaggtgc agataattaa     840
gaagaagctg gatcttagca acgtccagtc caagtgtggc tcaaaggata atatcaaaca     900
cgtcccggga ggcggcagtg tgagtacctt cacacgtccc atgcgccgtg ctgtggcttg     960
aattattagg aagtggtgtg agtgcgtaca cttgcgagac actgcataga ataaatcctt    1020
ctggatccac catggtggct tagatccggg catgtggaga cagagaagac tgttgagttt    1080
gtgataagca ctgactctct ctgcctattg gtctattttc cctccctcag tggcggtcga    1140
ggacaaactc tacgcggact tgccagtacg cttcgtgagc aagggcgagg agctgttcac    1200
cggggtggtg cccatcctgg tcgagctgga cggcgacgta aacggccaca agttcagcgt    1260
gtccggcgag ggcgagggcg acgccaccta cggcaagctg accctgaagt tcatctgcac    1320
caccggcaag ctgcccgtgc cctggcccac cctcgtgacc accctgacct acggcgtgca    1380
gtgcttcagc cgctaccccg accacctgaa gcagcacgac ttcttcaaga gtgcaatgcc    1440
cgaaggctac gtccaggagc gcaccatctt cttcaaggac gacggcaact acaagacccg    1500
cgccgaggtg aagttcgagg gcgacaccct ggtgaaccgc atcgagctga agggcatcga    1560
cttcaaggag gacggcaaca tcctggggca caagctggag tacaactaca acagccacaa    1620
cgtctatatc accgccgaca agcagaagaa cggcatcaag gtgaacttca agatccgcca    1680
caacatcgag gacggcagcg tgcagctcgc cgaccactac cagcagaaca cccccatcgg    1740
cgacggcccc gtgctgctgc ccgacaacca ctacctgagc acccagtccg ccctgagcaa    1800
agaccccaac gagaagcgcg atcatatggt cctgctggag ttcgtgaccg ccgccgggat    1860
cactctcggc accgacgagc tgtacaagta accggtcgcc accatggtga gcaagggcga    1920
ggagaataac atggccatca tcaaggagtt catgcgcttc aaggtgcgca tggagggctc    1980
cgtgaacggc cacgagttcg agatcgaggg cgagggcgag ggccgcccct acgagggcac    2040
ccagaccgcc aagctgaagg tgaccaaggg tggccccctg cccttcgcct gggacatcct    2100
aacccccaac ttcacctacg gctccaaggc ctacgtgaag caccccgccg acatccccga    2160
ctacttgaag ctgtccttcc ccgagggctt caagtgggag cgcgtgatga acttcgagga    2220
```

Figure 13

```
cggcggcgtg gtgaccgtga cccaggactc ctccctgcag gacggcgagt tcatctacaa    2280
ggtgaagctg cgcggcacca acttcccctc cgacggcccc gtaatgcaga agaagaccat    2340
gggctgggag gcctcctccg agcggatgta ccccgaggac ggcgccctga agggcgagat    2400
caagatgagg ctgaagctga aggacggcgg ccactacgac gctgaggtca agaccaccta    2460
caaggccaag aagcccgtgc agctgcccgg cgcctacatc gtcggcatca agttggacat    2520
cacctcccac aacgaggact acaccatcgt ggaactgtac gaacgcgccg agggccgcca    2580
ctccaccggc ggcatggacg agctgtataa gtaagcggcc gcgactctag atcataatca    2640
gccataccac atttgtagag gttttacttg ctttaaaaaa cctcccacac ctccccctga    2700
acctgaaaca taaaatgaat gcaattgttg ttgttaactt gtttattgca gcttataatg    2760
gttacaaata aagcaatagc atcacaaatt tcacaaataa agcatttttt tcactgcatt    2820
ctagttgtgg tttgtccaaa ctcatcaatg tatcttaagg cgtaaattgt aagcgttaat    2880
attttgttaa aattcgcgtt aaattttgt taaatcagct catttttaa ccaataggcc    2940
gaaatcggca aaatccctta taaatcaaaa gaatagaccg ataggggtt gagtgttgtt    3000
ccagtttgga acaagagtcc actattaaag aacgtggact ccaacgtcaa agggcgaaaa    3060
accgtctatc agggcgatgg cccactacgt gaaccatcac cctaatcaag ttttttgggg    3120
tcgaggtgcc gtaaagcact aaatcggaac cctaaaggga gccccgatt tagagcttga    3180
cggggaaagc cggcgaacgt ggcgagaaag gaagggaaga aagcgaaagg agcgggcgct    3240
agggcgctgg caagtgtagc ggtcacgctg cgcgtaacca ccacacccgc cgcgcttaat    3300
gcgccgctac agggcgcgtc aggtggcact tttcggggaa atgtgcgcgg aacccctatt    3360
tgtttatttt tctaaataca ttcaaatatg tatccgctca tgagacaata accctgataa    3420
atgcttcaat aatattgaaa aaggaagagt cctgaggcgg aaagaaccag ctgtggaatg    3480
tgtgtcagtt agggtgtgga aagtccccag gctccccagc aggcagaagt atgcaaagca    3540
tgcatctcaa ttagtcagca accaggtgtg gaaagtcccc aggctcccca gcaggcagaa    3600
gtatgcaaag catgcatctc aattagtcag caaccatagt cccgccccta actccgccca    3660
tcccgcccct aactccgccc agttccgccc attctccgcc ccatggctga ctaattttt    3720
ttatttatgc agaggccgag gccgcctcgg cctctgagct attccagaag tagtgaggag    3780
gcttttttgg aggcctaggc ttttgcaaag atcgatcaag agacaggatg aggatcgttt    3840
cgcatgattg aacaagatgg attgcacgca ggttctccgg ccgcttgggt ggagaggcta    3900
ttcggctatg actgggcaca acagacaatc ggctgctctg atgccgccgt gttccggctg    3960
tcagcgcagg ggcgcccggt tcttttgtc aagaccgacc tgtccggtgc cctgaatgaa    4020
ctgcaagacg aggcagcgcg gctatcgtgg ctggccacga cgggcgttcc ttgcgcagct    4080
gtgctcgacg ttgtcactga agcgggaagg gactggctgc tattgggcga agtgccgggg    4140
caggatctcc tgtcatctca ccttgctcct gccgagaaag tatccatcat ggctgatgca    4200
atgcggcggc tgcatacgct tgatccggct acctgcccat tcgaccacca agcgaaacat    4260
cgcatcgagc gagcacgtac tcggatggaa gccggtcttg tcgatcagga tgatctggac    4320
gaagagcatc aggggctcgc gccagccgaa ctgttcgcca ggctcaaggc gagcatgccc    4380
gacggcgagg atctcgtcgt gacccatggc gatgcctgct tgccgaatat catggtggaa    4440
aatggccgct tttctggatt catcgactgt ggccggctgg gtgtggcgga ccgctatcag    4500
gacatagcgt tggctacccg tgatattgct gaagagcttg gcggcgaatg ggctgaccgc    4560
```

Figure 13 – cont.

```
ttcctcgtgc tttacggtat cgccgctccc gattcgcagc gcatcgcctt ctatcgcctt    4620
cttgacgagt tcttctgagc gggactctgg ggttcgaaat gaccgaccaa gcgacgccca    4680
acctgccatc acgagatttc gattccaccg ccgccttcta tgaaaggttg ggcttcggaa    4740
tcgttttccg ggacgccggc tggatgatcc tccagcgcgg ggatctcatg ctggagttct    4800
tcgcccaccc tagggggagg ctaactgaaa cacggaagga gacaataccg gaaggaaccc    4860
gcgctatgac ggcaataaaa agacagaata aaacgcacgg tgttgggtcg tttgttcata    4920
aacgcggggt tcggtcccag ggctggcact ctgtcgatac cccaccgaga ccccattggg    4980
gccaatacgc ccgcgtttct tccttttccc cacccccaccc cccaagttcg ggtgaaggcc    5040
cagggctcgc agccaacgtc ggggcggcag gccctgccat agcctcaggt tactcatata    5100
tactttagat tgatttaaaa cttcattttt aatttaaaag gatctaggtg aagatccttt    5160
ttgataatct catgaccaaa atcccttaac gtgagttttc gttccactga gcgtcagacc    5220
ccgtagaaaa gatcaaagga tcttcttgag atccttttt tctgcgcgta atctgctgct    5280
tgcaaacaaa aaaaccaccg ctaccagcgg tggtttgttt gccggatcaa gagctaccaa    5340
ctcttttcc gaaggtaact ggcttcagca gagcgcagat accaaatact gtccttctag    5400
tgtagccgta gttaggccac cacttcaaga actctgtagc accgcctaca tacctcgctc    5460
tgctaatcct gttaccagtg gctgctgcca gtggcgataa gtcgtgtctt accgggttgg    5520
actcaagacg atagttaccg gataaggcgc agcggtcggg ctgaacgggg ggttcgtgca    5580
cacagcccag cttggagcga acgacctaca ccgaactgag atacctacag cgtgagctat    5640
gagaaagcgc cacgcttccc gaagggagaa aggcggacag gtatccggta agcggcaggg    5700
tcggaacagg agagcgcacg agggagcttc caggggaaa cgcctggtat ctttatagtc    5760
ctgtcgggtt tcgccacctc tgacttgagc gtcgattttt gtgatgctcg tcaggggggc    5820
ggagcctatg gaaaaacgcc agcaacgcgg ccttttacg gttcctggcc ttttgctggc    5880
cttttgctca catgttcttt cctgcgttat cccctgattc tgtggataac cgtattaccg    5940
```

Figure 13 — cont.

RNA INTERFERENCE MEDIATED THERAPY FOR NEURODEGENERATIVE DISEASES

This application is the U.S. national phase of International Application No. PCT/IB2016/051676 filed 24 Mar. 2016, which designated the U.S. and claims priority to IT Patent Application No. TO2015A000185 filed 25 Mar. 2015, the entire contents of each of which are hereby incorporated by reference.

FIELD OF THE INVENTION

The present invention concerns RNA interference mediated therapy for neurodegenerative diseases associated with abnormalities of microtubule-associated protein tau.

BACKGROUND OF THE INVENTION

Modulation of gene expression by endogenous, non-coding RNAs have been increasingly appreciated and known to play a role in eukaryotic development, and epigenetic control. Recently, methods have been developed to trigger RNA interference (RNAi) against specific targets in mammalian cells by introducing exogenously produced or intra-cellularly expressed small interfering RNA (siRNA) molecules.

These quick, inexpensive and effective methods have proven to be effective for knockdown experiments in vitro and in vivo. The ability to attain such selective gene silencing has led to the hypothesis that siRNAs can be used to suppress gene expression for therapeutic benefit. The ideal candidates for such an siRNA approach would be dominantly inherited diseases.

Recent studies by Miller V et al[1] have shown that siRNAs can be used to target untreatable neurodegenerative diseases such as polyglutamine (polyQ) neurodegeneration in Machado-Joseph disease, spinocerebellar ataxia type 3 (MJDSCA3) and Frontotemporal dementia with parkinsonism linked to chromosome 17 (FTDP-17). These studies have focused exclusively on selective silencing of the transcript produced by the mutant allele[1]. RNA interference has proven to be an efficient strategy for silencing mutant tau allele V337M, however, selective depletion of mutant allele was not completely achieved in the study because there was a partial depletion of the wild type allele of tau[1]. More recently, another example of MAPT-targeting siRNAs was described[2], wherein a mix of four siRNAs aimed at suppressing all tau isoforms in a mouse model of tauopathy was tested.

The MAPT (Microtubule associated protein tau) gene consists of 16 exons and its expression is regulated by complex alternative splicing. This results in the production of two types of alternatively spliced transcripts: one bearing Exon 10, also known as 4R (Four microtubule repeats) isoform and the other that lacks Exon 10 is called 3R isoform (Three microtubule repeats). Equal levels of these two isoforms are expressed in normal human adult brain. Though several mutations causing FTDP-17 are known in MAPT, a half of these affect alternative splicing of Exon 10. These include mis-sense mutations, silent mutations and point mutations which are located in Exon 10, introns 9 and 10. They are known to implicate an increase in Exon 10 causing an excessive accumulation of 4R. This leads to the formation of neurofibrillary tangles, hence resulting in neurodegeneration.

It is worth mentioning that abnormalities of tau are linked to the pathogenesis of neurodegenerative disease collectively termed as "tauopathies", and significantly elevated levels of tau are present in AD (Alzheimer's disease) brains.

A few approaches have been used for the correction of Exon 10 inclusion in FTDP-17:
 Small molecules: a screening has been performed which yielded cardiotonic steroids as exon 10 splicing modulator, albeit non-specific, drugs[3], and
 Antisense oligonucleotides for exon skipping: US-A-2003/0170704 by Stamm et al. relates to substances which are capable of controlling the inclusion of MAPT exon 10 (proteic splicing regulators or their cDNA, polypeptides controlling the phosphorylation of splicing regulators, or their cDNA, and antisense oligonucleotides which interact with the splice junctions of MAPT exon 10). Moreover, work by Kalbfuss et al.[4] has demonstrated that oligoribonucleotides binding to Exon 10 splicing junctions could suppress the predominant inclusion of Exon 10 in tau mRNA in the context of rat PC12 cells. However, recent work by Sud R et al[5] showed that targeting Exon 10 with antisense morpholino oligonucleotides did not yield exon-skipping in neuroblastoma cell lines. These authors claim that splicing regulation of exon 10 in cells expressing predominantly 4R isoform may vary from the neuroblastoma cell line in which the 3R isoform dominates.
 Trans-splicing of exon 10: RNA reprogramming using spliceosome-mediated RNA trans-splicing (SMaRT) was used to correct aberrant Exon 10 splicing resulting from FTDP-17 mutations in a minigene system in cells in culture[6]. This approach, however, is affected by low efficiency.

OBJECT AND SUMMARY OF THE INVENTION

The object of the present invention is to provide a therapeutic agent effective in the treatment of neurodegenerative diseases associated with abnormalities of MAPT gene encoded protein tau.

According to the invention, the above object is achieved thanks to the method specified in the ensuing claims, which are understood as forming an integral part of the present description.

In an embodiment, the instant disclosure discloses a therapeutic agent for use in the treatment of neurodegenerative diseases associated with abnormalities of MAPT gene encoded protein tau, wherein said therapeutic agent comprises one or more siRNA targeting MAPT gene exon 10 sequence (SEQ ID No.:1).

In a further embodiment, the instant disclosure provides for a method for the treatment of neurodegenerative diseases associated with abnormalities of MAPT gene encoded protein tau comprising administering to a patient who needs it of one or more siRNA, wherein the one or more siRNA comprise a sense strand comprising at least 19 continuous bases of mRNA corresponding to the MAPT exon 10 sequence of SEQ ID No.: 1 and an antisense strand comprising a sequence complementary thereto in an amount sufficient to make said treatment, wherein the one or more siRNA induce selective degradation of exon 10-containing MAPT transcripts.

In a still further embodiment, the instant disclosure concerns a pharmaceutical composition comprising one or more siRNA, wherein the one or more siRNA comprise a sense strand comprising at least 19 continuous bases of mRNA corresponding to the MAPT exon 10 sequence of SEQ ID No.: 1 and an antisense strand comprising a sequence complementary thereto and a pharmaceutically acceptable carrier.

BRIEF DESCRIPTION OF THE DRAWINGS

The invention will now be described, by way of example only, with reference to the enclosed figures of drawing, wherein:

FIG. 12. PFLARE 5A MAPT Exon 10 nucleotide sequence.

FIG. 13. PFLARE 5A MAPT MUT Exon 10 nucleotide sequence.

DETAILED DESCRIPTION OF THE INVENTION

Figure 1:
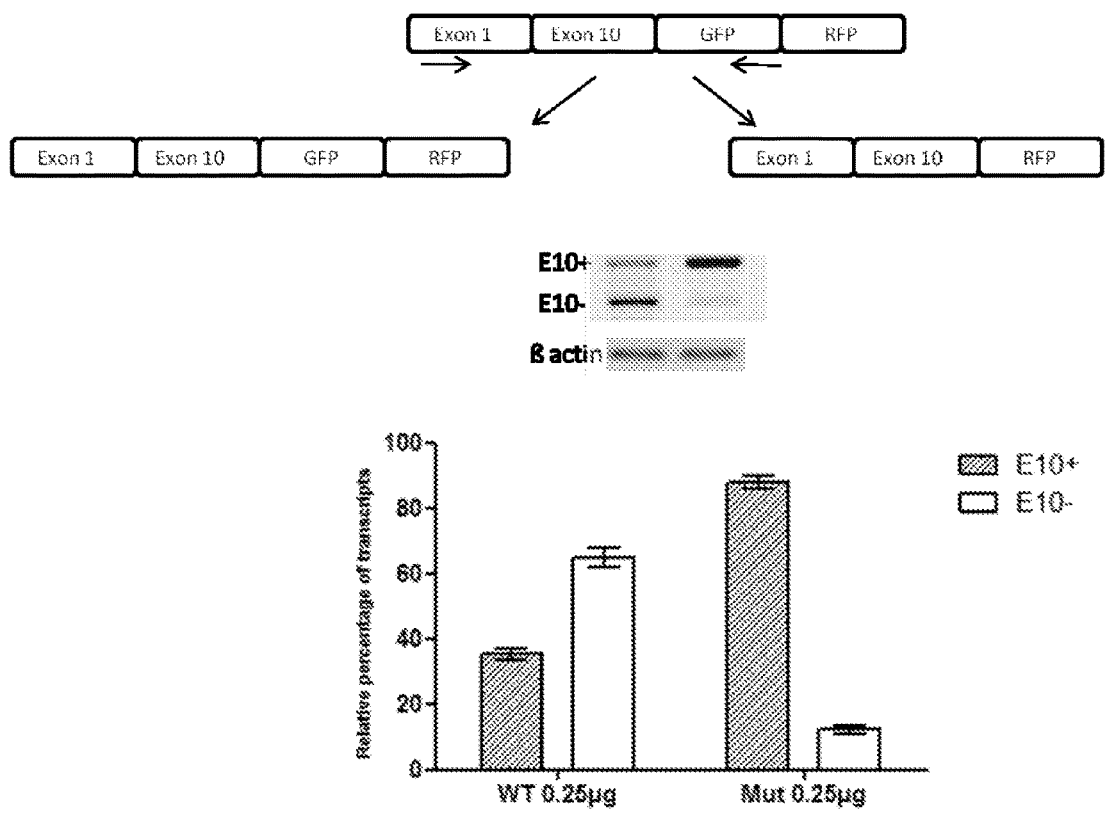
FIG. 1. Semi-quantitative RT-PCR analysis of levels of exon 10 in SH-SY5Y cells transfected with wild type and N279 mutant plasmid. The gel electrophoresis shows the RT-PCR products of transcripts of the minigenes, containing exon 10 (E10+, 290 bp) and without exon 10 (E10−, 210 bp). Histogram represents the densitometric units of each treatment condition normalised on β actin. Values represent mean SD± (n=3).

The invention will now be described in detail, by way of non limiting example, with reference to an RNA interference mediated therapy making use of a cell model recapitulating the Frontotemporal dementia with parkinsonism linked to chromosome 17 (FTDP-17) disease conditions. Nevertheless, the RNA interference mediated therapy herein disclosed can be used for the treatment of other neurodegenerative diseases associated with abnormalities in MAPT gene encoded protein tau, like for example Alzheimer's disease, Huntington's disease, type 1 myotonic dystrophy, and Parkinson's disease.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The present description concerns a therapeutic agent for use in the treatment of neurodegenerative diseases associated with abnormalities of MAPT gene encoded protein tau, wherein said therapeutic agent comprises one or more siRNAs targeting MAPT gene exon 10. Preferably, the therapeutic agent comprise a sense strand comprising at least 19 continuous bases of mRNA corresponding to the MAPT exon 10 sequence of SEQ ID No.: 1 and an antisense strand comprising a sequence complementary thereto.

In a further embodiment, the present description provides for use in the treatment of neurodegenerative diseases associated with abnormalities of MAPT gene encoded protein tau one or more siRNAs targeting MAPT gene exon 10, wherein the one or more siRNAs comprise a sense strand of 19-29 continuous bases of mRNA corresponding to the MAPT exon 10 sequence set forth in SEQ ID No.: 1 and an antisense strand comprising a sequence complementary thereto.

In a preferred embodiment, the present description concerns one or more siRNAs targeting MAPT gene exon 10 useful in the treatment of neurodegenerative diseases associated with abnormalities of MAPT gene encoded protein tau, wherein the one or more siRNAs are selected from i) a double strand RNA composed of a sense strand comprising a base sequence set forth in SEQ ID No.: 2, 4, 6, and an antisense strand comprising a sequence complementary thereto, which optionally has an overhang at the terminal of the sense strand and/or antisense strand, and ii) a double strand RNA composed of a sense strand comprising a base sequence wherein one to several bases have been added to and/or deleted from the 5' terminal and/or 3' terminal of the base sequence described in any one of SEQ ID No.: 2, 4, 6, and an antisense strand comprising a sequence complementary thereto, which optionally has an overhang at the terminal of the sense strand and/or antisense strand.

In a still further preferred embodiment, the instant description provides for one or more siRNAs targeting MAPT gene exon 10 able to induce selective degradation of exon 10-containing MAPT transcripts.

The neurodegenerative diseases associated with abnormalities of MAPT gene encoded protein tau that can benefit from the administration of one or more siRNAs targeting MAPT gene exon 10 are selected from Alzheimer disease, Huntington disease, type 1 myotonic dystrophy, Parkinson disease, frontotemporal dementia with parkinsonism linked to chromosome 17 (FTDP-17).

In a different embodiment, the description provides for a method of treatment of a neurodegenerative disease associated with abnormalities of MAPT gene encoded protein tau comprising administering to a patient who needs it of one or more siRNAs targeting MAPT gene exon 10, wherein the one or more siRNAs comprise a sense strand comprising at least 19 continuous bases of mRNA corresponding to the MAPT exon 10 sequence of SEQ ID No.: 1 and an antisense strand comprising a sequence complementary thereto in an amount sufficient to make said treatment, wherein the one or more siRNA induce selective degradation of exon 10-containing MAPT transcripts.

In a still further embodiment, the present description concerns a pharmaceutical composition comprising one or more siRNAs targeting MAPT gene exon 10, wherein the one or more siRNAs comprise a sense strand comprising at least 19 continuous bases of mRNA corresponding to the MAPT exon 10 sequence of SEQ ID No.: 1 and an antisense strand comprising a sequence complementary thereto and a pharmaceutically acceptable carrier.

The present disclosure shows the feasibility of an siRNA-based gene therapy to enable post-transcriptional gene silencing of Exon 10-containing MAPT transcripts in FTDP-17. A panel of siRNAs targeting tau mRNA containing Exon 10 have been designed, and tested in SH-SY5Y cells on a mutant minigene reporter plasmid in the context of N279 missense mutation (AAT to AAG) recapitulating FTDP-17 disease condition. Moreover, the 3 siRNAs were tested on NSC34 cells (a motor neuron-like cell line)[1] to validate the effects on endogenous condition with a predominant inclusion of Exon 10 (80%).

The effect of the siRNAs has been assayed using a high content imaging system. The results obtained through the screening assay have been further validated using an RT-PCR analysis. The effect on the endogenous Exon 10-containing MAPT transcripts has been tested using RT-PCR analysis.

In the instant description the Inventors designed a new approach for the restoration of a normal 4Rtau/3Rtau ratio, based on the use of siRNAs targeting MAPT exon 10 and inducing the selective degradation of the exon 10-containing MAPT transcripts. These siRNAs provide therapeutic benefit for FTDP-17 patients bearing mutations in MAPT exon 10 causing exon 10 inclusion, as the target sequences are not affected by the mutations.

The three siRNAs herein evaluated have the following nucleotide sequences:

```
siRNA A':
sense strand:
                        SEQ ID No.: 2
5'AGUCCAAGUGUGGCUCAAA3',
```

```
antisense strand:
                        SEQ ID No.: 3
5'UUUGAGCCACACUUGGACU3';

siRNA B':
sense strand:
                        SEQ ID No.: 4
5'GGCUCAAAGGAUAAUAUCA3', antisense strand:
                        SEQ ID No.: 5
5'UGAUAUUAUCCUUUGAGCC3';

siRNA C':
sense strand:
                        SEQ ID No.: 6
5'GCAACGUCCAGUCCAAGUG3', antisense strand:
                        SEQ ID No.: 7
5'CACUUGGACUGGACGUUGC3'.
```

Out of the 3 tested siRNAs (A, B and C), siRNA B shows maximum efficiency in transcript degradation. These results have been validated using a minigene recapitulating splicing mutation N279, and a similar effect is exhibited on NSC34[7,8] (a hybrid of mouse spinal cord motor neurons and neuroblastoma cell line) cells.

A recent review by Rettig and colleagues[9] has summarized the possible delivery approaches of the siRNA molecules and their success in clinical trials. The current development in the field and ongoing studies establishes the significance of these synthetic siRNAs, which may serve as potential therapeutics upon suitable delivery and administration.

Direct CNS (Central nervous system) administration is used as a method of choice in neurodegenerative diseases due to restricted entry across the blood brain barrier. Options of delivery include intrathecal, intraventricular, epidural and direct intratissue injection. Administration methods include long term infusions or through the use of mini pumps.

Chronic intraventricular pumps were used for the delivery of siRNAs against Amyloid precursor protein gene (App) to study Alzheimers related functions in adult mice. Efficient knockdowns were observed through potent siRNAs[10].

By employing naked and unassisted delivery of siRNAs in buffered saline, chronic infusion was performed in non-human primates to suppress levels of α synucein[11]. This protein is known to be associated with Parkinson's disease. Mini osmotic pumps were used for the direct infusion into the substantia nigra leading to a decrease in α synucein both at mRNA and protein levels.

siRNAs with modified PS linkages and 2'F-pyrimidine residues near the ends of each strand[12] were used for chronic infusion in to the CNS of SOD1 (G93A) mouse model of amyotrophic lateral sclerosis (ALS). Significant reduction of SOD1 mRNA was observed in the spinal cord. In the transgenic mouse model, an infusion over a 28 day period led to alleviated the progression of disease. The siRNAs were stable over the course of this period.

Cholesterol conjugated siRNAs[13] were used for the direct intrastriatal injection to target mutant Huntington gene (Htt) in the context of Huntington's disease.

The above mentioned strategies highlight the different modes of delivery of siRNAs and demonstrate efficacy in vivo.

Materials and Methods siRNAs

The following siRNAs—employed in the present experiments—were designed along the stretch of Exon (SEQ ID No.: 1), and produced by Eurofin Genomics, Ebersberg, Germany.

```
siRNA A:
sense strand:
                                   SEQ ID No.: 19
5'AGUCCAAGUGUGGCUCAAAdTdT3', antisense strand:
                                   SEQ ID No.: 20
5'UUUGAGCCACACUUGGACUdTdT3';

siRNA B:
sense strand:
                                   SEQ ID No.: 21
5'GGCUCAAAGGAUAAUAUCAdTdT3', antisense strand:
                                   SEQ ID No.: 22
5'UGAUAUUAUCCUUUGAGCCdTdT3';

siRNA C:
sense strand:
                                   SEQ ID No.: 23
5'GCAACGUCCAGUCCAAGUGdTdT3', antisense strand:
                                   SEQ ID No.: 24
5'CACUUGGACUGGACGUUGCdTdT3';

control siRNA:
sense strand:
                                   SEQ ID No : 8
5' UAAUGUAUUGGAACGCAUAdTdT3', antisense strand:
                                   SEQ ID No.: 9
5'UAUGCGUUCCAAUACAUUAdTdT3'.
```

The above siRNAs sequences differ from the SEQ ID NO.: 2 to 7 for the presence of an overhang consisting of two monophosphate deoxyribosylthymine (dT), which were introduced in SEQ ID No.: 2 to 7 at the 3' terminal in order to increase siRNA intracellular stability and efficiency thereof.

Figure 5:
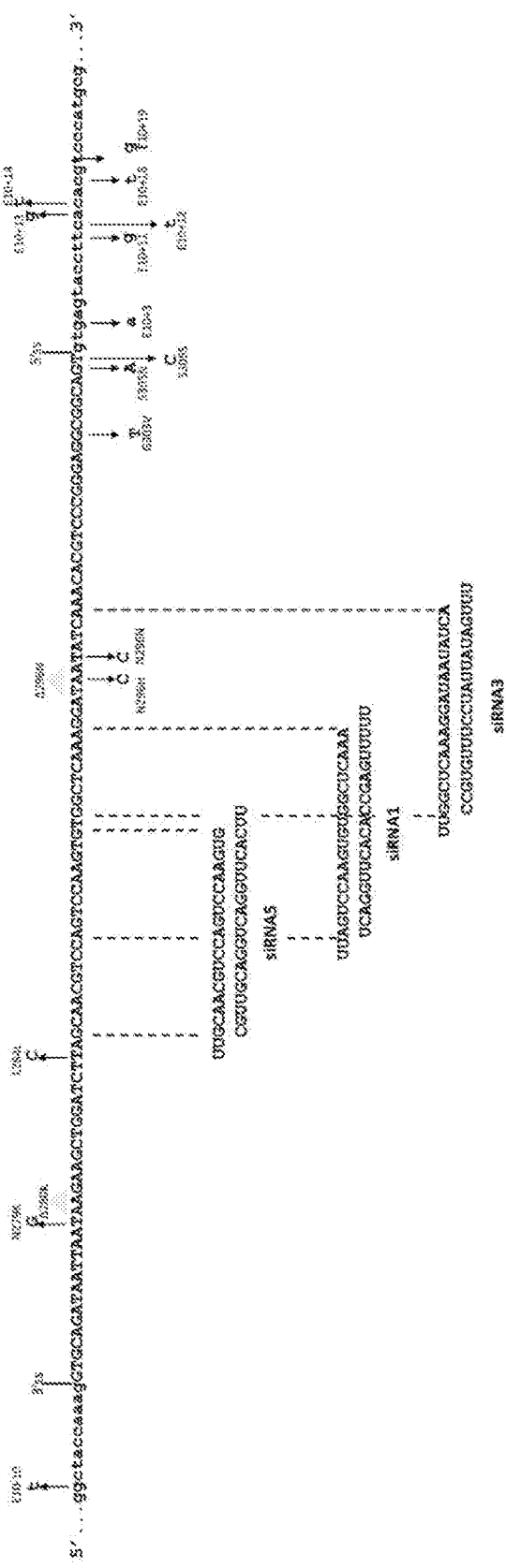
FIG. 5. Human tau E10 sequences (capitals) and flanking I9 and I10 sequences (lower case). The 5' and 3' splice sites are denoted by 5'ss and 3'ss, respectively. Only FTDP-17 mutations affecting E10 splicing are indicated. Deletions are denoted by shaded triangles. The sequences and target position of the three designed siRNAs are indicated.

FIG. 5 shows human tau E10 sequence (capitals—corresponding to SEQ ID No.: 1) and flanking I9 and I10 sequences (lower case); the human tau E10 sequence comprising flanking I9 (11 bases) and I10 (26 bases) sequences is provided in SEQ ID No.: 18. The 5' and 3' splice sites are denoted by 5'ss and 3'ss, respectively. Only FTDP-17 mutations affecting Exon 10 splicing are indicated. Deletions are denoted by shaded triangles. The sequences and target position of the three designed siRNAs A, B and C are provided.

SHYS5Y Cell Line

The SH-SY5Y cell line (ATCC-LGC standards, Teddington, UK; #CRL-2266) used for transfection experiments is a thrice cloned (SK-N-SH→SH-SY→SH-SY5→SH-SY5Y) subline of the neuroblastoma cell line SK-N-SH with a content of 15% Exon 10+ and 85% of Exon 10—in its transcript. The transfection efficiency (25% to 30%) in this cell line is comparatively higher than the other neuroblastoma cell lines. Therefore, this cell line was chosen to test the efficacy of siRNAs against endogenous Exon 10+ transcripts and for co-transfections of siRNAs with minigene reporter plasmids.

NSC-34 Cell Line

Mouse Motor neuron like hybrid cell line NSC-34 (Cellutions biosystems, Burlington, Ontario, Canada; #CLU140-A) was produced by fusion of motor neuron enriched, embryonic mouse spinal cord cells with mouse neuroblastoma[7,8]. The cultures contain two populations of cells: small, undifferentiated cells that have the capacity to undergo cell division and larger, multi-nucleate cells. These cells express many properties of motor neurons, including choline acetyltransferase, acetylcholine synthesis, storage and release and neurofilament triplet proteins. These cells can be differentiated using the all trans retinoic acid (atRA) thus establishing itself as a suitable model for the in vitro study of pathophysiology in motor neurons.

Mutagenesis of Fluorescent Reporter with Exon 10

The fluorescent reporter plasmid created by Peter Stoilov and colleagues[3], PFLARE 5A MAPT Exon 10 also referred to as the wild-type (WT) plasmid (SEQ ID No.: 10—FIG. 12), was mutated using the Quick change II site XL site-directed mutagenesis kit (Agilent Technologies, Santa Clara, Calif., USA; #200521) following the manufacturer's instructions. The following primers were designed such that they incorporated the nucleotide change of T to G.

```
Forward primer:
                                   SEQ ID No.: 11
5'ACCAAAGGTGCAGATAATTAAGAAG3'

Reverse primer:
                                   SEQ ID No.: 12
5'AGTTGCTAAGATCCAGCTTCTTCTT3'
```

The resulting plasmid PFLARE 5A MAPT MUT Exon 10 (SEQ ID No.: 13—FIG. 13) will be referred to as mutant N279 (Mut) plasmid.

Treatment of siRNA on Endogenous Condition

1. Transfection of SHYS5Y Cells and NSC-34 Cells with siRNAs

The transfection of SHYS5Y cells and NSC34 cells with siRNAs were performed using the Lipofectamine 3000 lipid based transfection reagent (Life Technologies-Invitrogen, Monza, Italy; #L3000-008).

1.1. Preparation of Cells 1.1.1) On the day before the experiment, $5 \times 10^4$ cells were seeded on a 24 well plate in 500 μl of complete medium without antibiotics at 37° C. in 5% $CO_2$.

1.2. Transfection of siRNAs 1.2.1) Transfections were performed as instructed by the manufacturer with 2 (μl) Lipofectamine 3000 for a range of siRNA concentration starting from 10 nM to 100 nM—in Opti-MEM medium without phenol red (Life Technologies-Gibco, Monza, Italy; #11058-021)—per well in a final volume of 500 μl.

1.2.2) As controls, cells were treated with Lipofectamine 3000 only (Mock) and transfected with Non-targeting siRNA (Non-specific controls—SEQ ID No.: 8 and 9).

1.2.3) Following transfection, the cells are incubated at 37° C. in 5% $CO_2$ for 48 hours.

1.2.4) The wells were then washed with PBS(1×) and Trizol reagent (Life Technologies, Monza, Italy; #15596-026) was used for the extraction of RNA following manufacturer's instructions for downstream analyses.

2. Co-Transfection of Reporter Plasmid and siRNAs in SHYS5Y Cells

2.1. Preparation of Cells 1.1) On the day before the experiment, $5 \times 10^4$ cells were seeded on a 24 well plate in 500 µl of complete medium (i.e. 1:1 mix of EMEM (Lonza #12-125F) and F12 NUTRIENT MIX (Life technologies-Gibco #1765-054) with 10% Fetal Bovine Serum (FBS)) without antibiotics at 37° C. in 5% $CO_2$. The 24 well plate format has been chosen to allow the recovery of a sufficient number of cells at the end of the assay after the image-based analysis, in order to perform downstream molecular analysis, such as RT-PCR and Western Blot.

2.2 Lipid-Based DNA and siRNA Co-Transfection 2.2.1) Transfections are performed as instructed by the manufacturer with a ratio of DNA (ng):Lipofectamine 3000 (µl) being 1:2 in Opti-MEM medium (GIBCO LIfetechnologies). The plasmids (SEQ ID No.: 10 and 13) are used at a concentration of 0.25 µg and 0.5 µg per well in a final volume of 500 µl.

2.2.2) Two different plasmid reporters (SEQ ID No.: 10, 13) are used for transfection namely the wild-type (WT) plasmid (SEQ ID No.: 10) and the mutant type (Mut) plasmid (SEQ ID No.: 13).

2.2.3) siRNAs (SEQ ID No.: 19 to 24) are used at the concentrations from 10 nM to 100 nM in a final volume of 500 µl per well.

3. High-Content Image Acquisition and Analysis
Preparation of Cells for Image Acquisition 3.1) Images of transfected cells were captured with a High content imaging system (Operetta, Perkin Elmer). 48 hours after transfection, the cells are incubated for 20 minutes at 37° C. in the presence of 1 mg/ml of Hoechst 33342 fluorescent dye. This allows counter-staining the nuclei which will enable the subsequent analyses.

Image Acquisition 3.2) Images were taken with a 20× LWD objective (Perkin Elmer #HH12940107), in combination with different filter sets: in particular a filter for Hoechst 3342 stain (excitation filter: 360-400 nm (Perkin Elmer #HH12000301); emission filter: 410-480 nm (Perkin Elmer #HH12000401)) is used to image the stained nuclei at 20 ms exposure time, whereas a combination of filters is used to measure the reporters' intensities: GFP (excitation filter: 460-490 nm (Perkin Elmer HH12000030); emission filter: 500-550 nm (Perkin Elmer #HH12000405)) and RFP (excitation filter: 520-550 nm (Perkin Elmer #HH12000305); emission filter: 560-630 nm (Perkin Elmer #HH12000410)), both at 200 ms exposure time.

Image Analysis 3.3) For the feature extraction protocol, cells were segmented and analyzed using the following workflow:

3.3.1) The first step is the identification of Nuclei, the primary objects of interest that are segmented by using the most suitable algorithm (phenoLOGIC™, PerkinElmer).

3.3.2) Assuming a homogeneous distribution of both GFP and RFP in the cells, the nuclear region was selected to quantify the mean fluorescence intensity in the two channels.

3.3.3) The sub-population of transfected cells was identified using a double-threshold strategy to filter out the cells being either positive for G(GFP) or for R(RFP) or for both.

3.3.4) Restricting the analysis to the transfected cells only, the ratio between the fluorescence properties G and R mean intensity is calculated on a per-cell basis. G/R is a parameter that indicates the prevalence of expression of one reporter over the other. Specifically, a low score indicates inclusion of the cassette exon, while a high one is connected with an efficient splicing of Exon 10.

3.3.5) An overview of the numerical properties of the cells can be visualized field by field in a scatter plot. Alternatively, to get a more complete representation of all the cells within a well, scatter plots or histograms of single cell properties can be created for representative wells of the WT and the Mut plasmid conditions. Such graphical representations allow a more accurate selection of an upper threshold J and a lower threshold K, distinguishing for cells preferentially expressing GFP (G/R>J), RFP (G/R<K) or equally expressing both the reporters (K<G/R<J) (FIG. 1). Harmony® high content imaging software (PerkinElmer) was employed.

3.4.6) The thresholds were then applied in a filter-based module to classify the cells in three different subpopulations. In synthesis, based on intensities emitted by the fluorescence signals, 3 read-outs were measured as a result of setting specific threshold values:cells expressing mainly GFP (G/R>J), cells expressing mainly RFP (G/R<K), cells equally expressing both the reporters (K<G/R<J).

3.4.7) Feature outputs include total cell count, transfected cells count and % calculated over the total number of cells, G/R median value of all the cells of the well, the % of cells preferentially expressing GFP (G/R>J), RFP (G/R<K) and equally expressing both the reporters (K<G/R<J).

3.4.8) Percentage of cell viability was calculated as follows: (total number of cells in transfected well/total number of cells in Mock)*100

4. RNA Extractions and RT-PCR 4.1) The wells were washed with 1×PBS and RNA was extracted from each well using Trizol reagent following manufacturer's instructions.

4.2) The extracted RNA was treated with DNase by using Turbo DNAse kit (Life technologies-Ambion #AM1907) according to the manufacturer's instructions.

4.3) 500 ng of the extracted RNA was reverse transcribed to cDNA with Revert Aid First Strand cDNA synthesis Kit (Thermoscientific #K1622) by using oligo dT18 oligonucleotides (a synthetic single-stranded 18-mer oligonucleotide with 5'- and 3'-hydroxyl ends, available in the kit), following manufacturer's protocol.

4.4) The cDNA obtained serves as a template for semi quantitative RT-PCR reactions to evaluate the expression of Exon 10 in these transcripts.

| PCR CYCLE: | |
|---|---|
| 10 min | 95° C. |
| 0:30 seconds | 95° C. |
| 0:40 seconds | 60° C. |
| 1 min | 72° C. |
| 10 min | 72° C. |
| ∞ | 4° C. |

4.4) The expression levels of Exon 10 containing transcripts are analyzed with the following primers:

```
Endogenous condition:
TAUR9F:
                                   SEQ ID No.: 14
5'CTGAAGCACCACCAGCCGGGAGG3', TAU13R:
                                   SEQ ID No.: 15
5'TGGTCTGTCTTGGCTTTGGC3'.

Plasmid reporters:
Exon 1 Bgl For:
                                   SEQ ID No.: 16
5'AAACAGATCTACCATTGGTGCACCTGACTCC3', EGFP Rev:
                                   SEQ ID No.: 17
5'CGTCGCCGTCCAGCTCGACCAG3'.
```

4.5) Amplified products are allowed to run with 100 bp DNA ladder (Fermentas) on a 2% Agarose gel electrophoresis (5% Ethidium Bromide) at 100 volts in 1×TBE running buffer for 40 minutes.

4.6) Densitometric analyses are performed with Image J software (an open architecture system using Java plugin) after image acquisition with BioDoc-It imaging system (UPV, Upland, Calif., USA).

Results

The siRNAs were tested for their efficacy on transfected reporter minigenes. Previous work by Stoilov P et al[3] has shown that the splicing of a two-color (Green/Red) fluorescent reporter plasmid with MAPT Exon 10 can be modulated using bioactive compounds. The reporter plasmid (SEQ ID No.: 10) was produced such that exon 10 inclusion favors the production of RFP (Red fluorescent protein) and exon 10 exclusion produces GFP (Green fluorescent protein) (FIG. 1). The reporter plasmid created by Stoilov and colleagues and termed as wild type reporter (as it recapitulated the endogenous condition of exon 10 content in the majority of neuroblastoma cell lines) was used (FIG. 1). The plasmid was further mutated to incorporate the N279 mutation to alter splicing (AAT to AAG), recapitulating FTDP-17 disease condition (SEQ ID No.: 13). This base change creates a purine-rich stretch (AAGAAGAAG), and resembles an exon splice-enhancer consensus; this alters splicing leading to exon 10 inclusion and subsequent production of RFP (FIG. 1).

Figure 2:
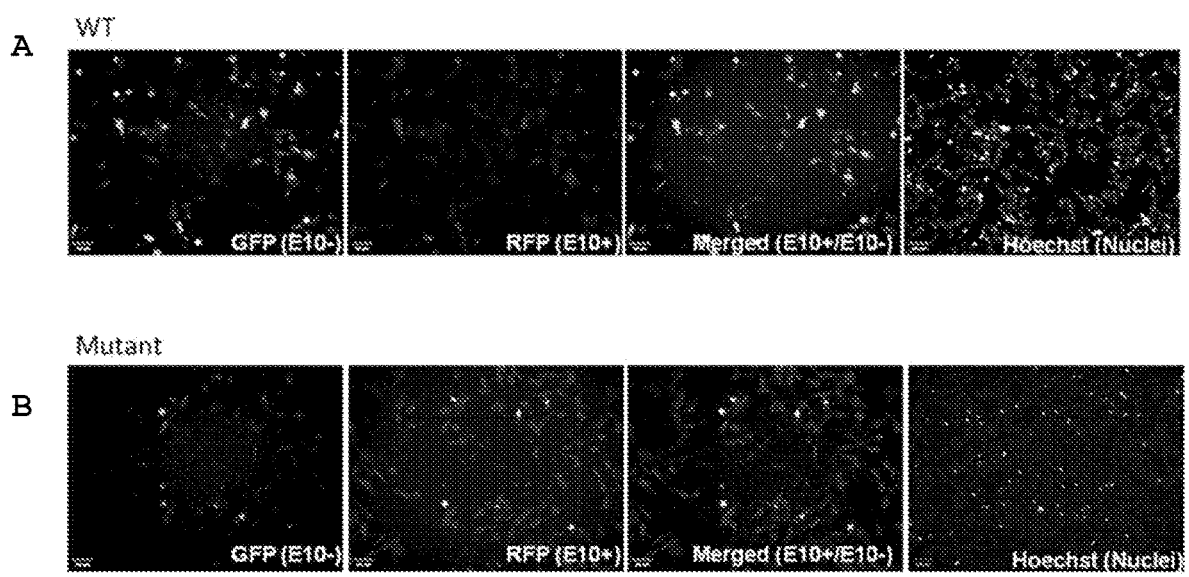
FIG. 2. Representative images of SH-SY5Y cell line transfected with 0.25 μg of either wild type plasmid or mutant plasmid. A) Wild type and B) Mutant N279 reporter plasmids.
Figure 3:
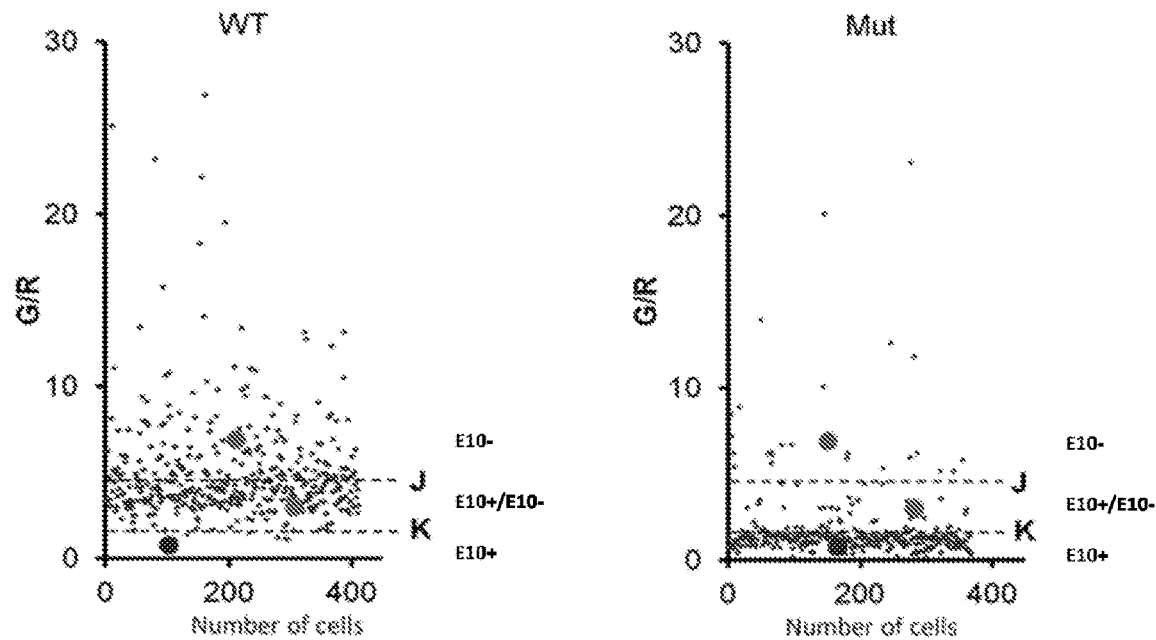
FIG. 3. Setting up of threshold values based on intensities of RFP and GFP. Scatter plots representing Green/Red (G/R) values of each cell in a particular well bearing one of the dual reporter plasmids (WT and Mut, respectively). The indicated thresholds are arbitrarily selected to classify the cell population in three different classes.
Figure 4:
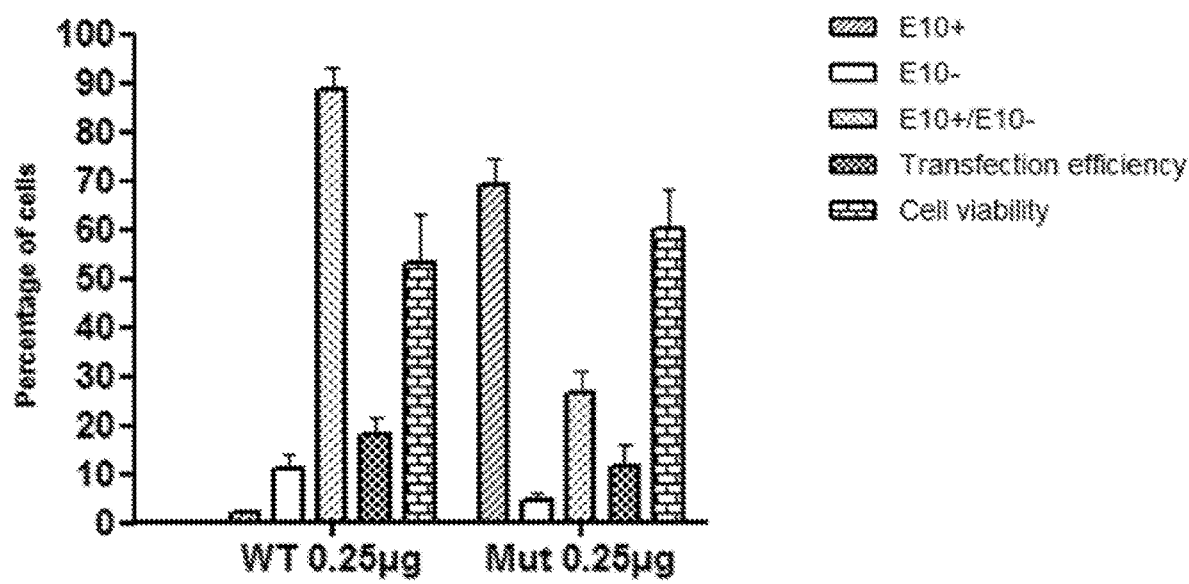
FIG. 4. Image based analysis of SHYS5Y cells transfected with Wild type and Mutant reporter plasmids. Histogram represents the selected read-outs of the quantitative analysis of the two reporters, such as the relative percentages of the three sub-populations of SHYS5Y cells classified by intensity properties, the transfection efficiency and the cell viability. Values represent mean±SD (n=3).

With the purpose of analyzing the effects of the siRNAs on the reporter minigenes, an image-based analysis to quantify the fluorescent reporters, obtaining single cell-based read-outs using an High Content Screening system, was developed by the present inventors. In brief, SH-SY5Y cell line was transfected with either wild type plasmid or mutant plasmid. The two plasmids ensure different percentages of exon 10 inclusion in the spliced transcript, which is evident from the difference in the number of red or green cells, and in their intensity (FIG. 2). The intensity of green and red fluorescence in the transfected cells was measured by an Operetta High Content Screening instrument, and the cells were grouped in three categories: red cells in which the majority of the transcript bears exon 10, green cells in which the majority of the transcript is devoid of exon 10, and yellow cells in which the proportion of the two splicing isoforms is around 1:1 (FIG. 3). By this analysis the point mutation in the reporter minigene (SEQ ID No.: 13) was assessed to shift splicing of Exon 10 thus altering the fluorescent signals from a relatively low level of RFP (2%) to a very high level (65%) due to Exon 10 inclusion (FIG. 3 and FIG. 4). Transfection efficiency was about 20% and cell viability about 60% (FIG. 4).

Three different exon 10-targeting siRNAs (SEQ ID Nos 19 to 24) spanning the exon 10 sequence have been designed on the basis of following rules: stretches of 4 or more bases (such as AAAA or CCCC), regions with GC content <30% or >60%, repeats and low complexity sequences, single nucleotide polymorphism (SNP) sites were avoided; a BLAST homology search was performed to avoid off-target effects on other genes or sequences (FIG. 5).

Figure 6:
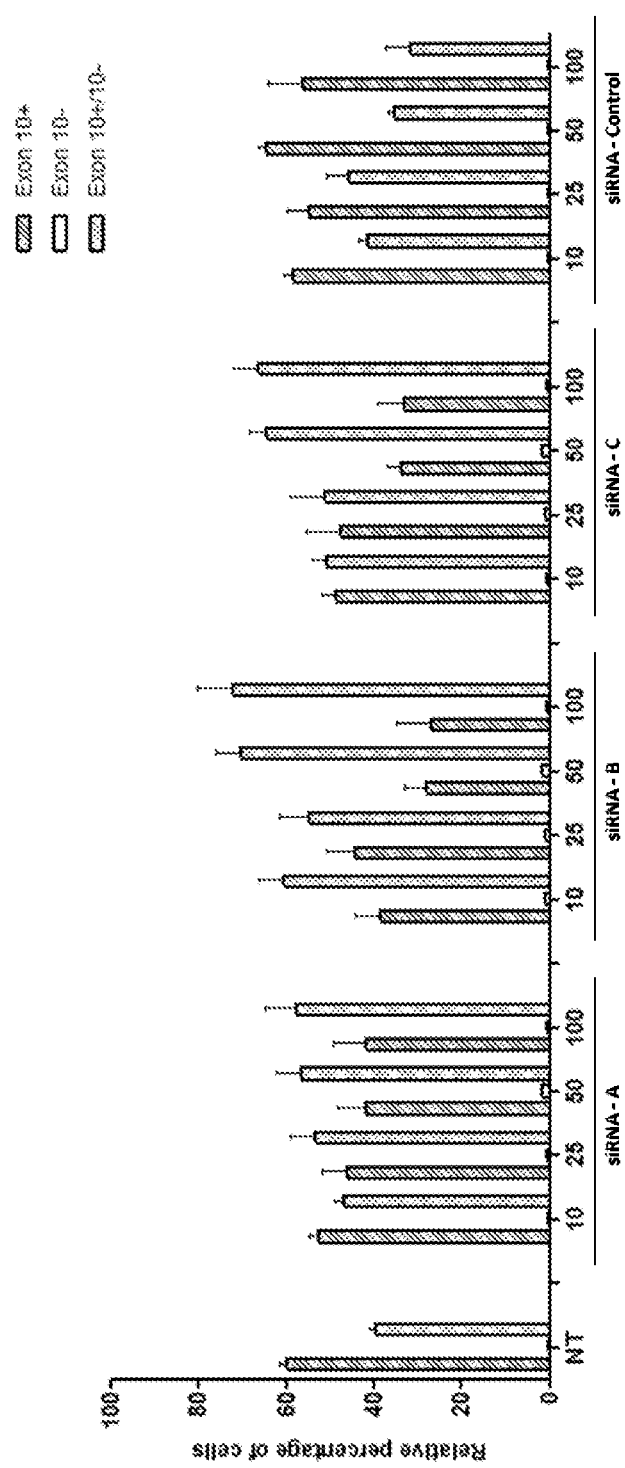
FIG. 6. An image based screening assay has been performed for the different siRNAs and compared to the values obtained with a control siRNA. siRNAs were cotransfected in SH-SY5Y cells together with 0.25 μg of mutant reporter minigene plasmid. The values represent mean±SD (n=3)
Figure 7:
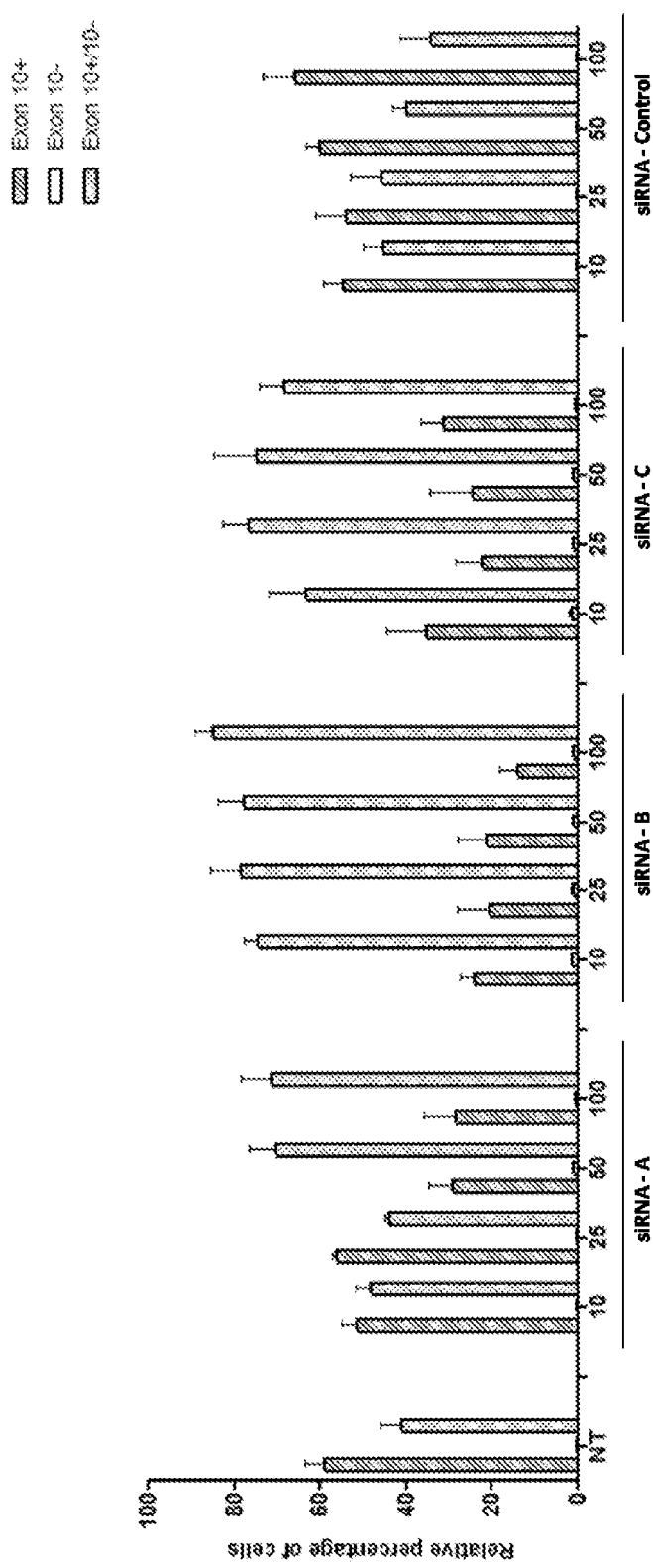
FIG. 7. An image based screening assay has been performed for the different siRNAs and compared to the values obtained with a control siRNA. siRNAs were cotransfected in SH-SY5Y cells together with 0.5 μg of mutant reporter minigene plasmid. The values represent mean±SD (n=3).
Figure 8:
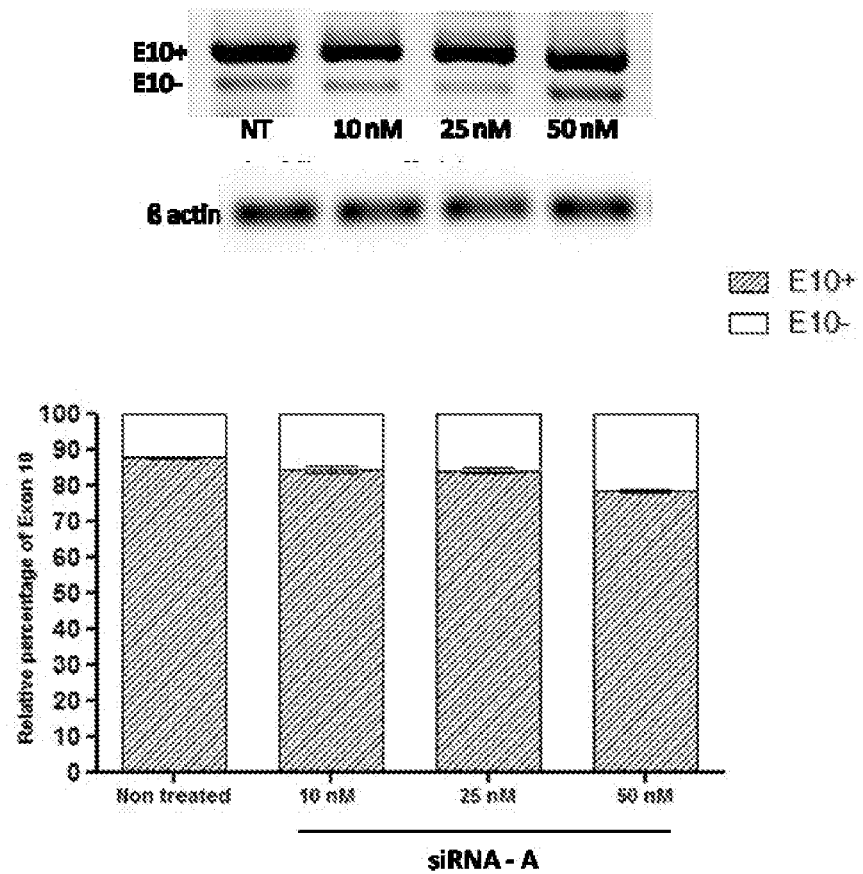
FIG. 8. Semi-quantitative RT-PCR analysis of SH-SY5Y cells transfected with the minigene reporter plasmid and siRNA A.
Figure 9:
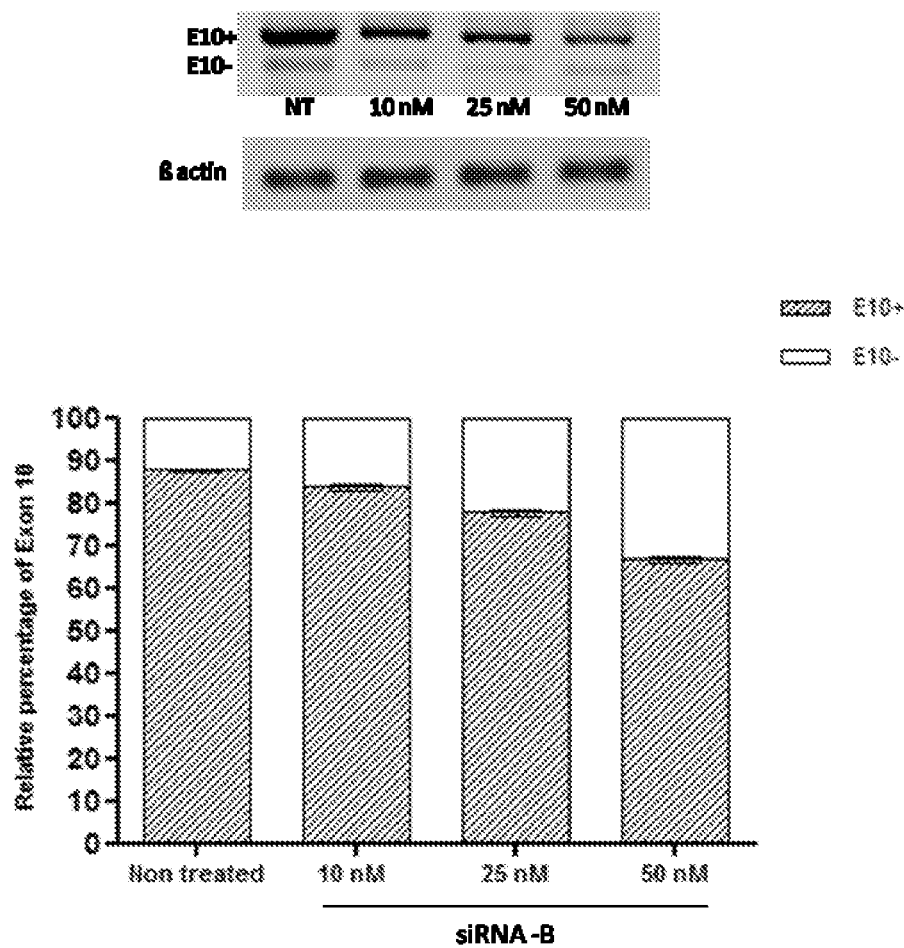
FIG. 9. Semi-quantitative RT-PCR analysis of SH-SY5Y cells transfected with the minigene reporter plasmid and siRNA B.
Figure 10:
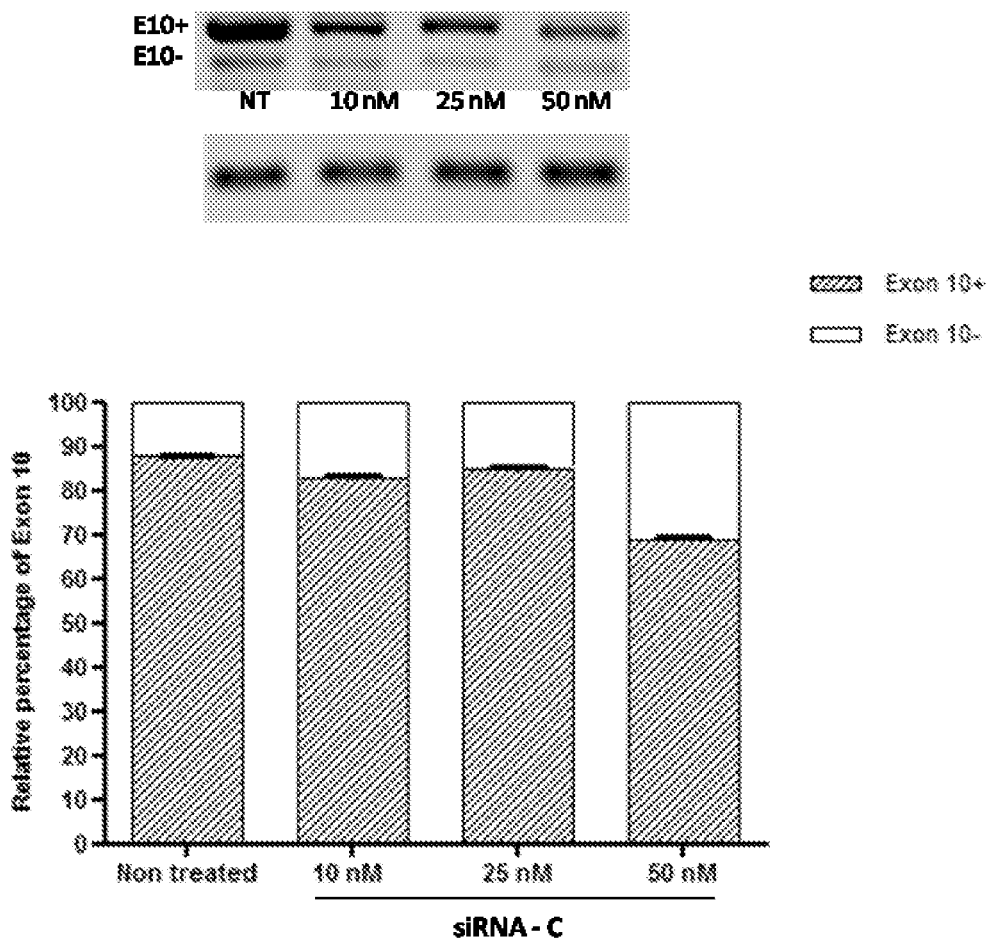
FIG. 10. Semi-quantitative RT-PCR analysis of SH-SY5Y cells transfected with the minigene reporter plasmid and siRNA C.

The efficacy of the three designed siRNAs was tested at increasing concentrations upon their co-transfection with either 0.5 μg (FIG. 6) or 0.25 μg of the mutant reporter minigene (FIG. 7). In both experimental designs siRNA A (SEQ ID No.: 19 and 20), siRNA B (SEQ ID No.: 21 and 22) and siRNA C (SEQ ID No.: 23 and 24) were effective in reducing the exon 10-containing transcript. siRNA B (SEQ ID No.: 21 and 22) appeared to be the most efficient siRNA, decreasing the red cells from 60% to 15% and increasing the yellow cells from 40% to 80% (FIG. 7). Semi-quantitative RT-PCR analysis confirmed the reduction of Exon 10 upon treatment with siRNA A (SEQ ID No.: 19 and 20, FIG. 8), siRNA B (SEQ ID No.: 20 and 22, FIG. 9) and siRNA C (SEQ ID No.: 23 and 24, FIG. 10) reaching ~10%, 25% and 20% reduction, respectively, upon treatment with a 50 nM concentration.

Figure 11:
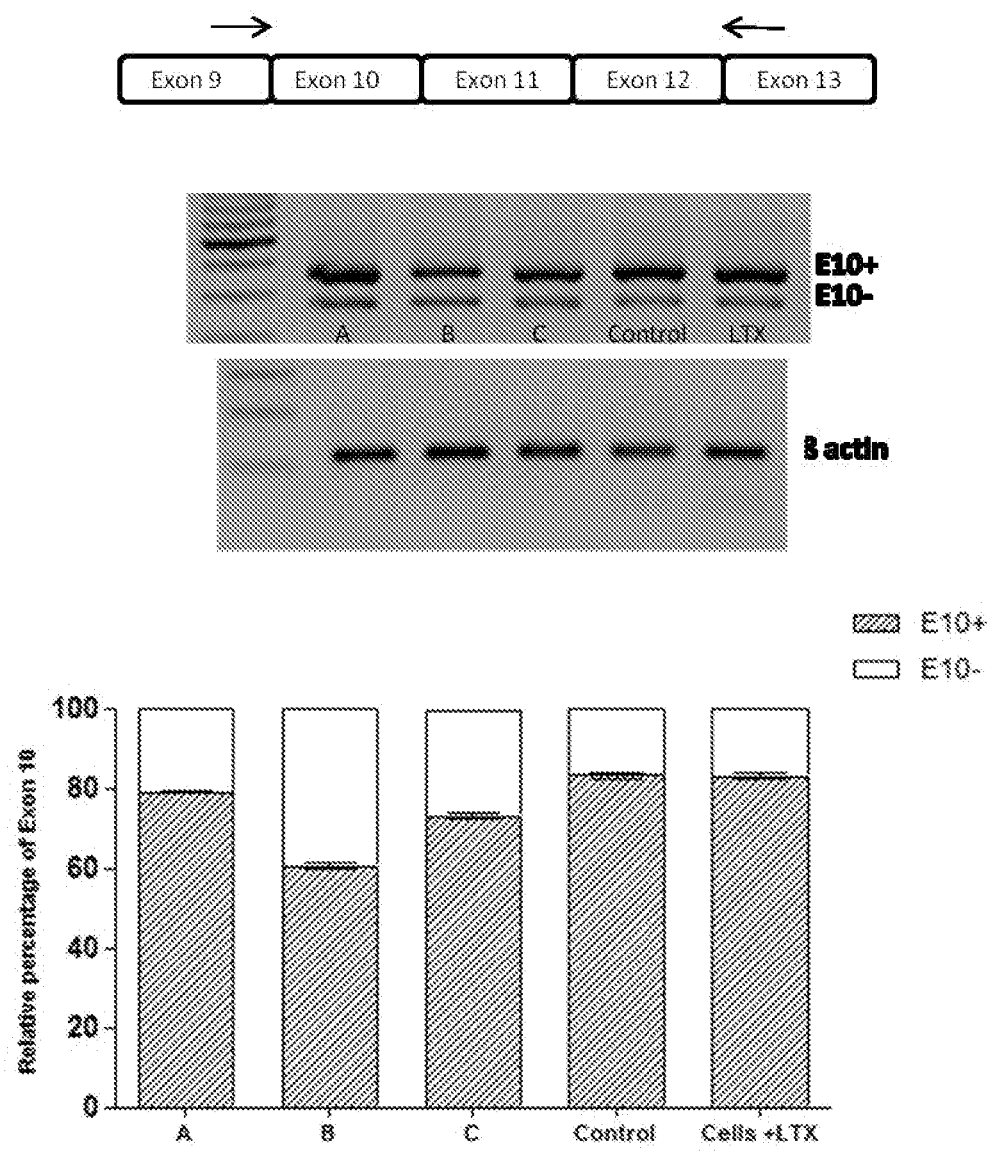
FIG. 11. Semi-quantitative RT-PCR of NSC34 cells transfected with three siRNAs or a control siRNA.

The effect of siRNA A (SEQ ID No.: 19 and 20), siRNA B (SEQ ID No.: 20 and 22) and siRNA C (SEQ ID No.: 23 and 24) on the endogenous MAPT transcript was tested upon their transfection in NSC34 cell line (FIG. 11). In NSC34 cells 83% of the endogenous MAPT transcript contains exon 10 and the remaining 17% is devoid of exon 10, thus serving as a suitable model for the study of effects of siRNA on Exon 10 containing transcripts in endogenous conditions (FIG. 11). RT-PCR analysis shows reduction of Exon 10+ endogenous transcripts upon treatment with siRNAs A (SEQ ID No.: 19 and 20) (6%), B (SEQ ID No.: 20 and 22) (28%) and C (SEQ ID No.: 23 and 24) (12%) at 50 nM concentration. In this model system, therefore, siRNA B appears the most effective siRNA in the selective degradation of exon 10-containing transcripts.

Naturally, while the principle of the invention remains the same, the details of construction and the embodiments may widely vary with respect to what has been described and illustrated purely by way of example, without departing from the scope of the present invention.

REFERENCES

1. Miller et al. Targeting Alzheimer's disease genes with RNA interference: an efficient strategy for silencing mutant alleles. *Nucl Acids Res* (2004) 32 (2): 661-668
2. Xu et al. Tau Silencing by siRNA in the P301S Mouse model of Tauopathy. *Curr Gene Ther* (2014); 14 (5):343-351.

3. Stoilov et al. A high-throughput screening strategy identifies cardiotonic steroids as alternative splicing modulators. *Proc Natl Acad Sci USA* (2008) 105 (32): 11218-23.
4. Kalbfuss et al. Correction of alternative splicing of tau in frontotemporal dementia and parkinsonism linked to chromosome 17. *J Biol Chem* (2001) 276: 42986-42993.
5. Sud et al. Antisense-mediated Exon Skipping Decreases Tau Protein Expression: A Potential Therapy For Tauopathies. *Mol Ther Nucleic Acids* (2014) July 29; 3: e180
6. Rodriguez-Martin et al. Correction of tau mis-splicing caused by FTDP-17 MAPT mutations by spliceosome-mediated RNA trans-splicing. *Hum Mol Genet* (2009) 18 (17): 3266-73.
7. Cashman et al. Neuroblastoma×spinal cord (NSC) hybrid cell lines resemble developing motor neurons. *Dev Dyn* (1992); 194 (3):209-21.
8. Maier et al. Differentiated NSC-34 motoneuron-like cells as experimental model for cholinergic neurodegeneration. *Neurochem Int* (2013) 62 (8): 1029-38
9. Rettig G R, Behlke M A Progress toward in vivo use of siRNAs-II *Mol Ther*. (2012) March; 20 (3):483-512.
10. Senechal et al. (2007). Amyloid precursor protein knockdown by siRNA impairs spontaneous alternation in adult mice. *J Neurochem* 102: 1928-1940.
11. McCormack et al. (2010). Alpha-synuclein suppression by targeted small interfering RNA in the primate substantia nigra. *PLoS ONE* 5: e12122.
12. Wang et al. (2008). Therapeutic gene silencing delivered by a chemically modified small interfering RNA against mutant SOD1 slows amyotrophic lateral sclerosis progression. *J Biol Chem* 283: 15845-15852.
13. DiFiglia et al. Therapeutic silencing of mutant huntingtin with siRNA attenuates striatal and cortical neuropathology and behavioral deficits. *Proc Natl Acad Sci USA* (2007) 104: 17204-17209.

The invention claimed is:

1. A therapeutic agent comprising one or more siRNAs targeting MAPT gene exon 10, wherein the one or more siRNAs comprise a double stranded RNA comprising:
   (1) a sense strand comprising a base sequence of SEQ ID NO.: 2, 4, or 6, wherein the sense strand comprises 19-29 continuous bases of mRNA corresponding to the MAPT gene exon 10 sequence set forth in SEQ ID NO.: 1; and
   (2) an antisense strand comprising a sequence complementary thereto,
   wherein the double stranded RNA optionally has a single stranded overhang at the terminal of the sense strand and/or antisense strand, and wherein the one or more siRNAs are capable of inducing the selective degradation of exon 10-containing MAPT transcripts.

2. A method for the treatment of a neurodegenerative disease associated with abnormalities of MAPT gene encoded protein tau comprising administering to a patient in need of said treatment a therapeutically effective amount of the therapeutic agent of claim 1.

3. A pharmaceutical composition comprising the therapeutic agent of claim 1 and a pharmaceutically acceptable carrier.

4. The therapeutic agent according to claim 1, wherein the region of complementarity between the sense strand and antisense strand consists of the sequence of SEQ ID NO.: 2, 4, or 6.

5. The therapeutic agent according to claim 1, wherein the sense strand consists of the sequence of SEQ ID NO.: 2, 4, or 6, and the antisense strand consists of a sequence complementary thereto.

6. The therapeutic agent according to claim 1, wherein the sense strand comprises the base sequence of SEQ ID NO.: 2.

7. The therapeutic agent according to claim 1, wherein the sense strand comprises the base sequence of SEQ ID NO.: 4.

8. The therapeutic agent according to claim 1, wherein the sense strand comprises the base sequence of SEQ ID NO.: 6.

9. The therapeutic agent according to claim 4, wherein the region of complementarity consists of the sequence of SEQ ID NO.: 2.

10. The therapeutic agent according to claim 4, wherein the region of complementarity consists of the sequence of SEQ ID NO.: 4.

11. The therapeutic agent according to claim 4, wherein the region of complementarity consists of the sequence of SEQ ID NO.: 6.

12. The therapeutic agent according to claim 5, wherein the sense strand consists of a base sequence of SEQ ID NO.: 2.

13. The therapeutic agent according to claim 5, wherein the sense strand consists of a base sequence of SEQ ID NO.: 4.

14. The therapeutic agent according to claim 5, wherein the sense strand consists of a base sequence of SEQ ID NO.: 6.

15. The therapeutic agent according to claim 4, wherein the double stranded RNA comprises a single stranded overhang at the 3' terminal end of the sense strand and the 3' terminal end of the antisense strand, wherein each of the overhangs consists of two monophosphate deoxyribosylthymine.

16. A method for the treatment of a neurodegenerative disease associated with abnormalities of MAPT gene encoded protein tau comprising administering to a patient in need of said treatment a therapeutically effective amount of the therapeutic agent of claim 4.

17. A method for the treatment of a neurodegenerative disease associated with abnormalities of MAPT gene encoded protein tau comprising administering to a patient in need of said treatment a therapeutically effective amount of the therapeutic agent of claim 5.

18. The method of claim 2 wherein the neurodegenerative disease associated with abnormalities of MAPT gene encoded protein tau is Alzheimer disease, Huntington disease, type 1 myotonic dystrophy, Parkinson disease, or frontotemporal dementia with parkinsonism linked to chromosome 17 (FTDP-17).

19. The method of claim 16 wherein the neurodegenerative disease associated with abnormalities of MAPT gene encoded protein tau is Alzheimer disease, Huntington disease, type 1 myotonic dystrophy, Parkinson disease, or frontotemporal dementia with parkinsonism linked to chromosome 17 (FTDP-17).

\* \* \* \* \*

SEQUENCE LISTING

<160> NUMBER OF SEQ ID NOS: 24

<210> SEQ ID NO 1
<211> LENGTH: 93
<212> TYPE: DNA
<213> ORGANISM: homo sapiens

<400> SEQUENCE: 1
gtgcagataa ttaataagaa gctggatctt agcaacgtcc agtccaagtg tggctcaaag      60
gataatatca aacacgtccc gggaggcggc agt                                   93

<210> SEQ ID NO 2
<211> LENGTH: 19
<212> TYPE: RNA
<213> ORGANISM: artificial
<220> FEATURE:
<223> OTHER INFORMATION: siRNA A' - sense strand

<400> SEQUENCE: 2
aguccaagug uggcucaaa                                                   19

<210> SEQ ID NO 3
<211> LENGTH: 19
<212> TYPE: RNA
<213> ORGANISM: artificial
<220> FEATURE:
<223> OTHER INFORMATION: siRNA A' - antisense strand

<400> SEQUENCE: 3
uuugagccac acuuggacu                                                   19

<210> SEQ ID NO 4
<211> LENGTH: 19
<212> TYPE: RNA
<213> ORGANISM: artificial
<220> FEATURE:
<223> OTHER INFORMATION: siRNA B' - sense strand

<400> SEQUENCE: 4
ggcucaaagg auaauauca                                                   19

<210> SEQ ID NO 5
<211> LENGTH: 19
<212> TYPE: RNA
<213> ORGANISM: artificial

```
<220> FEATURE:
<223> OTHER INFORMATION: siRNA B' - antisense strand

<400> SEQUENCE: 5
ugauauuauc cuuugagcc                                                    19

<210> SEQ ID NO 6
<211> LENGTH: 19
<212> TYPE: RNA
<213> ORGANISM: artificial
<220> FEATURE:
<223> OTHER INFORMATION: siRNA C' - sense strand

<400> SEQUENCE: 6
gcaacgucca guccaagug                                                    19

<210> SEQ ID NO 7
<211> LENGTH: 19
<212> TYPE: RNA
<213> ORGANISM: artificial
<220> FEATURE:
<223> OTHER INFORMATION: siRNA C' - antisense strand

<400> SEQUENCE: 7
cacuuggacu ggacguugc                                                    19

<210> SEQ ID NO 8
<211> LENGTH: 21
<212> TYPE: RNA
<213> ORGANISM: artificial
<220> FEATURE:
<223> OTHER INFORMATION: control siRNA - sense strand
<220> FEATURE:
<221> NAME/KEY: misc_feature
<222> LOCATION: (20)..(21)
<223> OTHER INFORMATION: n stands for deoxyribosylthymine (dT)

<400> SEQUENCE: 8
uaauguauug gaacgcauan n                                                 21

<210> SEQ ID NO 9
<211> LENGTH: 21
<212> TYPE: RNA
<213> ORGANISM: artificial
<220> FEATURE:
<223> OTHER INFORMATION: control siRNA - antisense strand
<220> FEATURE:
<221> NAME/KEY: misc_feature
<222> LOCATION: (20)..(21)
<223> OTHER INFORMATION: n stands for deoxyribosylthymine (dT)

<400> SEQUENCE: 9
uaugcguucc aauacauuan n                                                 21

<210> SEQ ID NO 10
<211> LENGTH: 5948
<212> TYPE: DNA
<213> ORGANISM: artificial
<220> FEATURE:
<223> OTHER INFORMATION: WT PFLARE PLASMID

<400> SEQUENCE: 10
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
```

```
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctaccatt ggtgcacctg actcctgagg agaagtctgc cgttactgcc    660
ctgtggggca aggtgaacgt ggaagagttg gtggtgaggc cctgggccac cagtaagtat    720
caaggttaca agacaggttt aaggagacca atagaaactg ggcatgtgga cagagaaag    780 actcttgggt ttctgaattc ctcatccttt tttctggcta ccaaaggtgc agataattaa    840
taagaagctg gatcttagca acgtccagtc caagtgtggc tcaaaggata atatcaaaca    900
cgtcccggga ggcggcagtg tgagtacctt cacacgtccc atgcgccgtg ctgtggcttg    960
aattattagg aagtggtgtg agtgcgtaca cttgcgagac actgcataga ataaatcctt   1020
ctggatccac catggtggct tagatccggg catgtggaga cagagaagac tgttgagttt   1080
gtgataagca ctgactctct ctgcctattg gtctattttc cctccctcag tggcggtcga   1140
ggacaaactc tacgcggact tgccagtacg cttcgtgagc aagggcgagg agctgttcac   1200
cggggtggtg cccatcctgg tcgagctgga cggcgacgta aacggccaca agttcagcgt   1260
gtccggcgag ggcgagggcg acgccaccta cggcaagctg accctgaagt tcatctgcac   1320
caccggcaag ctgcccgtgc cctggcccac cctcgtgacc accctgacct acggcgtgca   1380
gtgctttagc cgctacccg accacctgaa gcagcacgac ttcttcaaga gtgcaatgcc   1440
cgaaggctac gtccaggagc gcaccatctt cttcaaggac gacggcaact acaagacccg   1500
cgccgaggtg aagttcgagg gcgacaccct ggtgaaccgc atcgagctga agggcatcga   1560
cttcaaggag gacggcaaca tcctggggca caagctggag tacaactaca acagccacaa   1620
cgtctatatc accgccgaca gcagaagaa cggcatcaag gtgaacttca gatccgcca   1680 caacatcgag gacggcagcg tgcagctcgc cgaccactac cagcagaaca cccccatcgg   1740
cgacggcccc gtgctgctgc ccgacaacca ctacctgagc acccagtccg ccctgagcaa   1800
agaccccaac gagaagcgcg atcatatggt cctgctggag ttcgtgaccg ccgccgggat   1860
cactctcggc accgacgagc tgtacaagta accggtcgcc accatggtga gcaagggcga   1920
ggagaataac atggccatca tcaaggagtt catgcgcttc aaggtgcgca tggagggctc   1980
cgtgaacggc cacgagttcg agatcgaggg cgagggcgag ggccgcccct acgagggcac   2040
ccagaccgcc aagctgaagg tgaccaaggg tggccccctg cccttcgcct gggacatcct   2100 aaccccccaac ttcacctacg gctccaaggc ctacgtgaag caccccgccg acatccccga   2160
ctacttgaag ctgtccttcc ccgagggctt caagtgggag cgcgtgatga acttcgagga   2220
cggcggcgtg gtgaccgtga cccaggactc ctccctgcag gacggcgagt tcatctacaa   2280
ggtgaagctg cgcggcacca acttcccctc cgacggcccc gtaatgcaga agaagaccat   2340
gggctgggag gcctcctccg agcggatgta ccccgaggac ggcgccctga agggcgagat   2400
caagatgagg ctgaagctga aggacggcgg ccactacgac gctgaggtca agaccaccta   2460
caaggccaag aagcccgtgc agctgcccgg cgcctacatc gtcggcatca agttggacat   2520
cacctcccac aacgaggact acaccatcgt ggaactgtac gaacgcgccg agggccgcca   2580
```

```
ctccaccggc ggcatggacg agctgtataa gtaagcggcc gcgactctag atcataatca    2640
gccataccac atttgtagag gttttacttg ctttaaaaaa cctcccacac ctcccctga     2700 acctgaaaca taaatgaat gcaattgttg ttgttaactt gtttattgca gcttataatg     2760
gttacaaata aagcaatagc atcacaaatt tcacaaataa agcattttt tcactgcatt     2820 ctagttgtgg tttgtccaaa ctcatcaatg tatcttaagg cgtaaattgt aagcgttaat    2880
attttgttaa aattcgcgtt aaattttgt taaatcagct catttttaa ccaataggcc      2940 gaaatcggca aaatcccta taaatcaaaa gaatagaccg atagggtt gagtgttgtt       3000 ccagtttgga acaagagtcc actattaaag aacgtggact ccaacgtcaa agggcgaaaa    3060
accgtctatc agggcgatgg cccactacgt gaaccatcac cctaatcaag ttttttgggg    3120
tcgaggtgcc gtaaagcact aaatcggaac cctaaaggga gccccgatt tagagcttga    3180 cggggaaagc cggcgaacgt ggcgagaaag gaagggaaga aagcgaaagg agcgggcgct   3240
agggcgctgg caagtgtagc ggtcacgctg cgcgtaacca ccacacccgc cgcgcttaat   3300
gcgccgctac agggcgcgtc aggtggcact tttcggggaa atgtgcgcgg aacccctatt   3360
tgtttatttt tctaaataca ttcaaatatg tatccgctca tgagacaata accctgataa   3420
atgcttcaat aatattgaaa aaggaagagt cctgaggcgg aaagaaccag ctgtggaatg   3480
tgtgtcagtt agggtgtgga aagtccccag gctccccagc aggcagaagt atgcaaagca   3540
tgcatctcaa ttagtcagca accaggtgtg gaaagtcccc aggctcccca gcaggcagaa   3600
gtatgcaaag catgcatctc aattagtcag caaccatagt cccgcccta actccgccca    3660 tcccgcccct aactccgccc agttccgccc attctccgcc ccatggctga ctaatttttt   3720
ttatttatgc agaggccgag gccgcctcgg cctctgagct attccagaag tagtgaggag   3780
gcttttttgg aggcctaggc ttttgcaaag atcgatcaag agacaggatg aggatcgttt   3840
cgcatgattg aacaagatgg attgcacgca ggttctccgg ccgcttgggt ggagaggcta   3900
ttcggctatg actgggcaca acagacaatc ggctgctctg atgccgccgt gttccggctg   3960
tcagcgcagg ggcgcccggt tctttttgtc aagaccgacc tgtccggtgc cctgaatgaa   4020
ctgcaagacg aggcagcgcg gctatcgtgg ctggccacga cgggcgttcc ttgcgcagct   4080
gtgctcgacg ttgtcactga agcgggaagg gactggctgc tattgggcga agtgccgggg   4140
caggatctcc tgtcatctca ccttgctcct gccgagaaag tatccatcat ggctgatgca   4200
atgcggcggc tgcatacgct tgatccggct acctgcccat tcgaccacca agcgaaacat   4260
cgcatcgagc gagcacgtac tcggatggaa gccggtcttg tcgatcagga tgatctggac   4320
gaagagcatc aggggctcgc gccagccgaa ctgttcgcca ggctcaaggc gagcatgccc   4380 gacgcgagg atctcgtcgt gacccatggc gatgcctgct tgccgaatat catggtggaa   4440
aatggccgct tttctggatt catcgactgt ggccggctgg gtgtggcgga ccgctatcag   4500
gacatagcgt tggctacccg tgatattgct gaagagcttg gcggcgaatg ggctgaccgc   4560
ttcctcgtgc tttacggtat cgccgctccc gattcgcagc gcatcgcctt ctatcgcctt   4620
cttgacgagt tcttctgagc gggactctgg ggttcgaaat gaccgaccaa gcgacgccca   4680
acctgccatc acgagatttc gattccaccg ccgccttcta tgaaaggttg gcttcggaa    4740 tcgttttccg gacgccggc tggatgatcc tccagcgcgg ggatctcatg ctggagttct    4800
tcgcccaccc taggggagg ctaactgaaa cacggaagga caataccg gaaggaaccc      4860 gcgctatgac ggcaataaaa agacagaata aaacgcacgg tgttgggtcg tttgttcata   4920
```

```
aacgcggggt tcggtcccag ggctggcact ctgtcgatac ccaccgaga ccccattggg    4980
gccaatacgc ccgcgtttct tccttttccc cacccaccc cccaagttcg ggtgaaggcc    5040
cagggctcgc agccaacgtc ggggcggcag gccctgccat agcctcaggt tactcatata    5100
tactttagat tgatttaaaa cttcattttt aatttaaaag gatctaggtg aagatccttt    5160
ttgataatct catgaccaaa atcccttaac gtgagttttc gttccactga gcgtcagacc    5220
ccgtagaaaa gatcaaagga tcttcttgag atcctttttt tctgcgcgta atctgctgct    5280
tgcaaacaaa aaaaccaccg ctaccagcgg tggtttgttt gccggatcaa gagctaccaa    5340
ctcttttttcc gaaggtaact ggcttcagca gagcgcagat accaaatact gtccttctag    5400
tgtagccgta gttaggccac cacttcaaga actctgtagc accgcctaca tacctcgctc    5460
tgctaatcct gttaccagtg gctgctgcca gtggcgataa gtcgtgtctt accgggttgg    5520
actcaagacg atagttaccg gataaggcgc agcggtcggg ctgaacgggg ggttcgtgca    5580
cacagcccag cttggagcga acgacctaca ccgaactgag atacctacag cgtgagctat    5640
gagaaagcgc cacgcttccc gaagggagaa aggcggacag gtatccggta agcggcaggg    5700
tcggaacagg agagcgcacg agggagcttc caggggggaaa cgcctggtat ctttatagtc    5760
ctgtcgggtt tcgccacctc tgacttgagc gtcgattttt gtgatgctcg tcagggggggc    5820
ggagcctatg gaaaaacgcc agcaacgcgg ccttttacg gttcctggcc ttttgctggc    5880
cttttgctca catgttcttt cctgcgttat cccctgattc tgtggataac cgtattaccg    5940
ccatgcat                                                             5948

<210> SEQ ID NO 11
<211> LENGTH: 24
<212> TYPE: DNA
<213> ORGANISM: artificial
<220> FEATURE:
<223> OTHER INFORMATION: Forward primer - per production of PFLARE 5A
      MUT Exon 10

<400> SEQUENCE: 11
ccaaaggtgc agataattaa gaag                                            24

<210> SEQ ID NO 12
<211> LENGTH: 24
<212> TYPE: DNA
<213> ORGANISM: artificial
<220> FEATURE:
<223> OTHER INFORMATION: Reverse primer - per production of PFLARE 5A
      MUT Exon 10

<400> SEQUENCE: 12
gttgctaaga tccagcttct tctt                                            24

<210> SEQ ID NO 13
<211> LENGTH: 5940
<212> TYPE: DNA
<213> ORGANISM: artificial
<220> FEATURE:
<223> OTHER INFORMATION: MUT PFLARE PLASMID

<400> SEQUENCE: 13
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
```

```
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctaccatt ggtgcacctg actcctgagg agaagtctgc cgttactgcc    660
ctgtggggca aggtgaacgt ggaagagttg gtggtgaggc cctgggccac cagtaagtat    720
caaggttaca agacaggttt aaggagacca atagaaactg ggcatgtgga gacagagaag    780
actcttgggt ttctgaattc ctcatccttt tttctggcta ccaaaggtgc agataattaa    840
gaagaagctg gatcttagca acgtccagtc caagtgtggc tcaaaggata atatcaaaca    900
cgtcccggga ggcggcagtg tgagtacctt cacacgtccc atgcgccgtg ctgtggcttg    960
aattattagg aagtggtgtg agtgcgtaca cttgcgagac actgcataga ataaatcctt   1020
ctggatccac catggtggct tagatccggg catgtgagga cagagaagac tgttgagttt   1080
gtgataagca ctgactctct ctgcctattg gtctattttc cctccctcag tggcggtcga   1140
ggacaaactc tacgcggact tgccagtacg cttcgtgagc aagggcgagg agctgttcac   1200
cggggtggtg cccatcctgg tcgagctgga cggcgacgta aacggccaca gttcagcgt   1260 gtccggcgag ggcgagggcg acgccaccta cggcaagctg accctgaagt tcatctgcac   1320
caccggcaag ctgcccgtgc cctggcccac cctcgtgacc accctgacct acggcgtgca   1380
gtgctttagc cgctaccccg accacctgaa gcagcacgac ttcttcaaga gtgcaatgcc   1440
cgaaggctac gtccaggagc gcaccatctt cttcaaggac gacggcaact acaagacccg   1500
cgccgaggtg aagttcgagg gcgacaccct ggtgaaccgc atcgagctga agggcatcga   1560
cttcaaggag gacggcaaca tcctggggca caagctggag tacaactaca acagccacaa   1620
cgtctatatc accgccgaca gcagaagaa cggcatcaag gtgaacttca agatccgcca   1680
caacatcgag gacggcagcg tgcagctcgc cgaccactac cagcagaaca cccccatcgg   1740
cgacggcccc gtgctgctgc ccgacaacca ctacctgagc acccagtccg ccctgagcaa   1800
agaccccaac gagaagcgcg atcatatggt cctgctggag ttcgtgaccg ccgccgggat   1860
cactctcggc accgacgagc tgtacaagta accggtcgcc accatggtga gcaagggcga   1920
ggagaataac atggccatca tcaaggagtt catgcgcttc aaggtgcgca tggagggctc   1980
cgtgaacggc cacgagttcg agatcgaggg cgagggcgag ggccgcccct acgagggcac   2040
ccagaccgcc aagctgaagg tgaccaaggg tggccccctg cccttcgcct gggacatcct   2100
aacccccaac ttcacctacg gctccaaggc ctacgtgaag caccccgccg acatccccga   2160
ctacttgaag ctgtccttcc ccgagggctt caagtgggag cgcgtgatga acttcgagga   2220
cggcggcgtg gtgaccgtga cccaggactc ctccctgcag gacggcgagt tcatctacaa   2280
ggtgaagctg cgcggcacca acttcccctc cgacggcccc gtaatgcaga agaagaccat   2340
gggctgggag gcctcctccg agcggatgta ccccgaggac ggcgccctga agggcagat   2400 caagatgagg ctgaagctga aggacggcgg ccactacgac gctgaggtca agaccaccta   2460
caaggccaag aagcccgtgc agctgcccgg cgcctacatc gtcggcatca gttggacat   2520 cacctcccac aacgaggact acaccatcgt ggaactgtac gaacgcgccg agggccgcca   2580
```

```
ctccaccggc ggcatggacg agctgtataa gtaagcggcc gcgactctag atcataatca    2640
gccataccac atttgtagag gttttacttg cttaaaaaa cctcccacac ctcccctga     2700
acctgaaaca taaatgaat gcaattgttg ttgttaactt gtttattgca gcttataatg    2760
gttacaaata aagcaatagc atcacaaatt tcacaaataa agcatttttt tcactgcatt   2820
ctagttgtgg tttgtccaaa ctcatcaatg tatcttaagg cgtaaattgt aagcgttaat   2880
attttgttaa aattcgcgtt aaattttgt taaatcagct catttttaa ccaataggcc     2940
gaaatcggca aaatcccta taaatcaaaa gaatagaccg atagggtt gagtgttgtt      3000
ccagtttgga acaagagtcc actattaaag aacgtggact ccaacgtcaa agggcgaaaa   3060
accgtctatc agggcgatgg cccactacgt gaaccatcac cctaatcaag tttttggg    3120
tcgaggtgcc gtaaagcact aaatcggaac cctaaaggga gccccgatt tagagcttga   3180
cggggaaagc cggcgaacgt ggcgagaaag gaagggaaga agcgaaagg agcgggcgct   3240
agggcgctgg caagtgtagc ggtcacgctg cgcgtaacca ccacaccgc cgcgcttaat   3300
gcgccgctac agggcgcgtc aggtggcact tttcggggaa atgtgcgcgg aaccctatt   3360
tgtttatttt tctaaataca ttcaaatatg tatccgctca tgagacaata accctgataa  3420
atgcttcaat aatattgaaa aaggaagagt cctgaggcgg aaagaaccag ctgtggaatg  3480
tgtgtcagtt agggtgtgga aagtccccag gctccccagc aggcagaagt atgcaaagca  3540
tgcatctcaa ttagtcagca accaggtgtg gaaagtcccc aggctcccca gcaggcagaa  3600
gtatgcaaag catgcatctc aattagtcag caaccatagt cccgccccta actccgccca  3660
tcccgcccct aactccgccc agttccgccc attctccgcc ccatggctga ctaattttt   3720
ttatttatgc agaggccgag gccgcctcgg cctctgagct attccagaag tagtgaggag  3780
gcttttttgg aggcctaggc ttttgcaaag atcgatcaag agacaggatg aggatcgttt  3840
cgcatgattg aacaagatgg attgcacgca ggttctccgg ccgcttgggt ggagaggcta  3900
ttcggctatg actgggcaca acagacaatc ggctgctctg atgccgccgt gttccggctg  3960
tcagcgcagg ggcgcccggt tctttttgtc aagaccgacc tgtccggtgc cctgaatgaa  4020
ctgcaagacg aggcagcgcg gctatcgtgg ctggccacga cgggcgttcc ttgcgcagct  4080
gtgctcgacg ttgtcactga agcgggaagg gactggctgc tattgggcga agtgccgggg  4140
caggatctcc tgtcatctca ccttgctcct gccgagaaag tatccatcat ggctgatgca  4200
atgcggcggc tgcatacgct tgatccggct acctgcccat tcgaccacca agcgaaacat  4260
cgcatcgagc gagcacgtac tcggatggaa gccggtcttg tcgatcagga tgatctggac  4320
gaagagcatc aggggctcgc gccagccgaa ctgttcgcca ggctcaaggc gagcatgccc  4380
gacggcgagg atctcgtcgt gacccatggc gatgcctgct tgccgaatat catggtggaa  4440
aatggccgct tttctggatt catcgactgt ggccggctgg gtgtggcgga ccgctatcag  4500
gacatagcgt tggctacccg tgatattgct gaagagcttg gcggcgaatg ggctgaccgc  4560
ttcctcgtgc tttacggtat cgccgctccc gattcgcagc gcatcgcctt ctatcgcctt  4620
cttgacgagt tcttctgagc gggactctgg ggttcgaaat gaccgaccaa gcgacgccca  4680
acctgccatc acgagatttc gattccaccg ccgccttcta tgaaaggttg gcttcggaa   4740
tcgtttccg gacgccggc tggatgatcc tccagcgcgg ggatctcatg ctggagttct   4800
tcgcccaccc tagggggagg ctaactgaaa cacggaagga acaataccg gaaggaaccc   4860
gcgctatgac ggcaataaaa agacagaata aaacgcacgg tgttgggtcg tttgttcata  4920
aacgcggggt tcggtcccag ggctggcact ctgtcgatac cccaccgaga ccccattggg  4980
```

```
gccaatacgc ccgcgtttct tccttttccc cacccccaccc cccaagttcg ggtgaaggcc      5040
cagggctcgc agccaacgtc ggggcggcag gccctgccat agcctcaggt tactcatata      5100
tactttagat tgatttaaaa cttcattttt aatttaaaag gatctaggtg aagatccttt      5160
ttgataatct catgaccaaa atcccttaac gtgagttttc gttccactga gcgtcagacc      5220
ccgtagaaaa gatcaaagga tcttcttgag atcctttttt tctgcgcgta atctgctgct      5280
tgcaaacaaa aaaaccaccg ctaccagcgg tggtttgttt gccggatcaa gagctaccaa      5340 ctcttttcc gaaggtaact ggcttcagca gagcgcagat accaaatact gtccttctag      5400
tgtagccgta gttaggccac cacttcaaga actctgtagc accgcctaca tacctcgctc      5460
tgctaatcct gttaccagtg gctgctgcca gtggcgataa gtcgtgtctt accgggttgg      5520
actcaagacg atagttaccg gataaggcgc agcggtcggg ctgaacgggg ggttcgtgca      5580
cacagcccag cttggagcga acgacctaca ccgaactgag atacctacag cgtgagctat      5640
gagaaagcgc cacgcttccc gaagggagaa aggcggacag gtatccggta agcggcaggg      5700
tcggaacagg agagcgcacg agggagcttc caggggggaaa cgcctggtat ctttatagtc      5760
ctgtcgggtt tcgccacctc tgacttgagc gtcgattttt gtgatgctcg tcagggggggc      5820 ggagcctatg gaaaaacgcc agcaacgcgg ccttttacg gttcctggcc ttttgctggc      5880
cttttgctca catgttcttt cctgcgttat cccctgattc tgtggataac cgtattaccg      5940
```

<210> SEQ ID NO 14
<211> LENGTH: 23
<212> TYPE: DNA
<213> ORGANISM: artificial
<220> FEATURE:
<223> OTHER INFORMATION: TAUR9F

<400> SEQUENCE: 14
ctgaagcacc accagccggg agg                                              23

<210> SEQ ID NO 15
<211> LENGTH: 20
<212> TYPE: DNA
<213> ORGANISM: artificial
<220> FEATURE:
<223> OTHER INFORMATION: TAU13R

<400> SEQUENCE: 15
tggtctgtct tggctttggc                                                  20

<210> SEQ ID NO 16
<211> LENGTH: 31
<212> TYPE: DNA
<213> ORGANISM: artificial
<220> FEATURE:
<223> OTHER INFORMATION: Plasmid reporter - Exon 1 Bgl For

<400> SEQUENCE: 16
aaacagatct accattggtg cacctgactc c                                     31

<210> SEQ ID NO 17
<211> LENGTH: 22
<212> TYPE: DNA
<213> ORGANISM: artificial
<220> FEATURE:
<223> OTHER INFORMATION: Plasmid reporter - EGFP Rev

<400> SEQUENCE: 17
cgtcgccgtc cagctcgacc ag                                              22

<210> SEQ ID NO 18
<211> LENGTH: 130
<212> TYPE: DNA
<213> ORGANISM: homo sapiens

<400> SEQUENCE: 18
ggctaccaaa ggtgcagata attaataaga agctggatct tagcaacgtc cagtccaagt    60
gtggctcaaa ggataatatc aaacacgtcc cgggaggcgg cagtgtgagt accttcacac   120
gtcccatgcg                                                          130

<210> SEQ ID NO 19
<211> LENGTH: 21
<212> TYPE: DNA
<213> ORGANISM: artificial
<220> FEATURE:
<223> OTHER INFORMATION: siRNA A - sense strand with overhang
<220> FEATURE:
<221> NAME/KEY: misc_feature
<222> LOCATION: (20)..(21)
<223> OTHER INFORMATION: n stands for deoxyribosylthymine (dT)

<400> SEQUENCE: 19
aguccaagug uggcucaaan n                                               21

<210> SEQ ID NO 20
<211> LENGTH: 21
<212> TYPE: DNA
<213> ORGANISM: artificial
<220> FEATURE:
<223> OTHER INFORMATION: siRNA A - antisense strand with overhang
<220> FEATURE:
<221> NAME/KEY: misc_feature
<222> LOCATION: (20)..(21)
<223> OTHER INFORMATION: n stands for deoxyribosylthymine (dT)

<400> SEQUENCE: 20
uuugagccac acuuggacun n                                               21

<210> SEQ ID NO 21
<211> LENGTH: 21
<212> TYPE: DNA
<213> ORGANISM: artificial
<220> FEATURE:
<223> OTHER INFORMATION: siRNA B - sense strand with overhang
<220> FEATURE:
<221> NAME/KEY: misc_feature
<222> LOCATION: (20)..(21)
<223> OTHER INFORMATION: n stands for deoxyribosylthymine (dT)

<400> SEQUENCE: 21
ggcucaaagg auaauaucan n                                               21

<210> SEQ ID NO 22
<211> LENGTH: 21
<212> TYPE: DNA
<213> ORGANISM: artificial
<220> FEATURE:
<223> OTHER INFORMATION: siRNAB - antisense strand with overhang
<220> FEATURE:
<221> NAME/KEY: misc_feature
<222> LOCATION: (20)..(21)
<223> OTHER INFORMATION: n stands for deoxyribosylthymine (dT)

<400> SEQUENCE: 22
ugauauuauc cuuugagccn n                                               21

```
<210> SEQ ID NO 23
<211> LENGTH: 21
<212> TYPE: DNA
<213> ORGANISM: artificial
<220> FEATURE:
<223> OTHER INFORMATION: siRNA C - sense strand with overhang
<220> FEATURE:
<221> NAME/KEY: misc_feature
<222> LOCATION: (20)..(21)
<223> OTHER INFORMATION: n stands for deoxyribosylthymine (dT)

<400> SEQUENCE: 23
gcaacgucca guccaagugn n                                        21

<210> SEQ ID NO 24
<211> LENGTH: 21
<212> TYPE: DNA
<213> ORGANISM: artificial
<220> FEATURE:
<223> OTHER INFORMATION: siRNA C - antisense strand with overhang
<220> FEATURE:
<221> NAME/KEY: misc_feature
<222> LOCATION: (20)..(21)
<223> OTHER INFORMATION: n stands for deoxyribosylthymine (dT)

<400> SEQUENCE: 24
cacuuggacu ggacguugcn n                                        21
```